US012599058B2

(12) United States Patent
Ji et al.

(10) Patent No.: US 12,599,058 B2
(45) Date of Patent: Apr. 14, 2026

(54) METHODS AND SYSTEMS FOR GENERATING FERTILIZER FORMULAS

(71) Applicant: INSTITUTE OF SOIL, FERTILIZER, RESOURCES AND ENVIRONMENT OF JIANGXI ACADEMY OF AGRICULTURAL SCIENCES, Nanchang (CN)

(72) Inventors: Jianhua Ji, Nanchang (CN); Xianjin Lan, Nanchang (CN); Zhenzhen Lyu, Nanchang (CN); Hongqian Hou, Nanchang (CN); Xiumei Liu, Nanchang (CN); Yiren Liu, Nanchang (CN); Zijun Wang, Nanchang (CN)

(73) Assignee: INSTITUTE OF SOIL, FERTILIZER, RESOURCES AND ENVIRONMENT OF JIANGXI ACADEMY OF AGRICULTURAL SCIENCES, Nanchang (CN)

( * ) Notice: Subject to any disclaimer, the term of this patent is extended or adjusted under 35 U.S.C. 154(b) by 460 days.

(21) Appl. No.: 18/468,678

(22) Filed: Sep. 15, 2023

(65) Prior Publication Data

US 2024/0090369 A1 Mar. 21, 2024

(30) Foreign Application Priority Data

Sep. 16, 2022 (CN) .......................... 202211127615.1

(51) Int. Cl.
| | |
|---|---|
| *A01C 21/00* | (2006.01) |
| *G16C 20/30* | (2019.01) |
| *G16C 20/50* | (2019.01) |
| *G16C 20/70* | (2019.01) |

(52) U.S. Cl.
CPC ............ *A01C 21/007* (2013.01); *G16C 20/30* (2019.02); *G16C 20/50* (2019.02); *G16C 20/70* (2019.02)

(58) Field of Classification Search
CPC ...... A01C 21/007; G16C 20/70; G16C 20/30; G16C 20/50; Y02P 60/21
See application file for complete search history.

(56) References Cited

U.S. PATENT DOCUMENTS

| | | | |
|---|---|---|---|
| 12,071,385 B2 * | 8/2024 | Babu | C05G 3/44 |
| 12,366,678 B2 * | 7/2025 | Cisek | G01N 33/24 |

* cited by examiner

*Primary Examiner* — An H Do
(74) *Attorney, Agent, or Firm* — PORUS IP LLC

(57) ABSTRACT

Embodiments of the present disclosure provide a method and system for generating a fertilizer formula, the method is executed by a processor, comprising: obtaining a basic formula for fertilization; obtaining monitoring data based on a monitoring device; determining a soil feature of a predetermined point based on the monitoring data; determining an experiment scheme and experimental parameters based on the soil feature and an experimental design; determining a fertilization dosage and conducting an intelligent planting experiment based on the fertilization dosage and the basic formula for fertilization; obtaining experimental parameters and experimental yield data of each experimental processing, and optimized yield data of an optimized fertilization processing, and storing the experimental parameters, experimental yield data, and the optimized yield data in a storage unit; and determining a model for reduced fertilization of nitrogen, phosphorus, and potassium nutrients and generating the fertilizer formula based on a regression model.

20 Claims, 4 Drawing Sheets

100

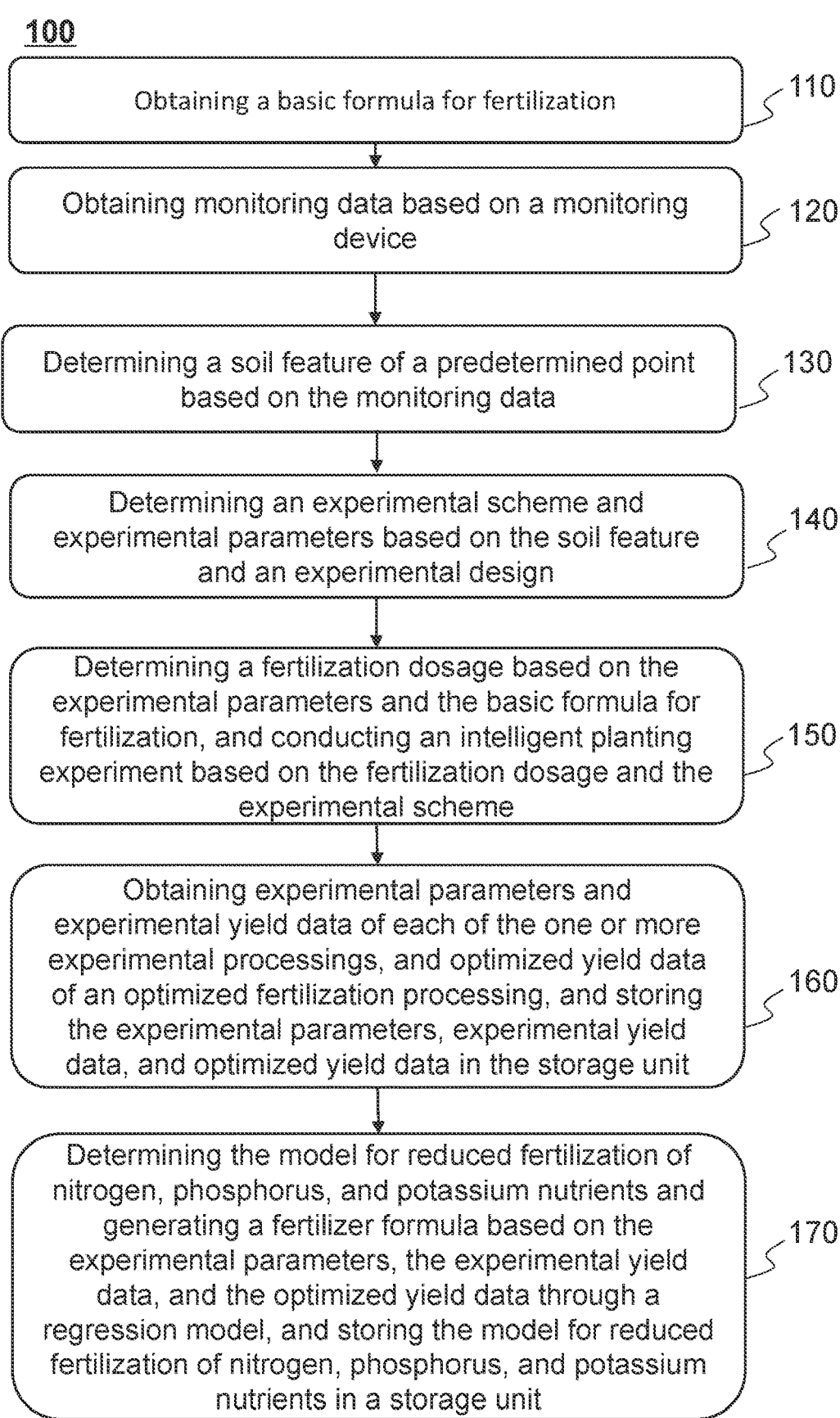

Obtaining a basic formula for fertilization — 110

Obtaining monitoring data based on a monitoring device — 120

Determining a soil feature of a predetermined point based on the monitoring data — 130

Determining an experimental scheme and experimental parameters based on the soil feature and an experimental design — 140

Determining a fertilization dosage based on the experimental parameters and the basic formula for fertilization, and conducting an intelligent planting experiment based on the fertilization dosage and the experimental scheme — 150

Obtaining experimental parameters and experimental yield data of each of the one or more experimental processings, and optimized yield data of an optimized fertilization processing, and storing the experimental parameters, experimental yield data, and optimized yield data in the storage unit — 160

Determining the model for reduced fertilization of nitrogen, phosphorus, and potassium nutrients and generating a fertilizer formula based on the experimental parameters, the experimental yield data, and the optimized yield data through a regression model, and storing the model for reduced fertilization of nitrogen, phosphorus, and potassium nutrients in a storage unit — 170

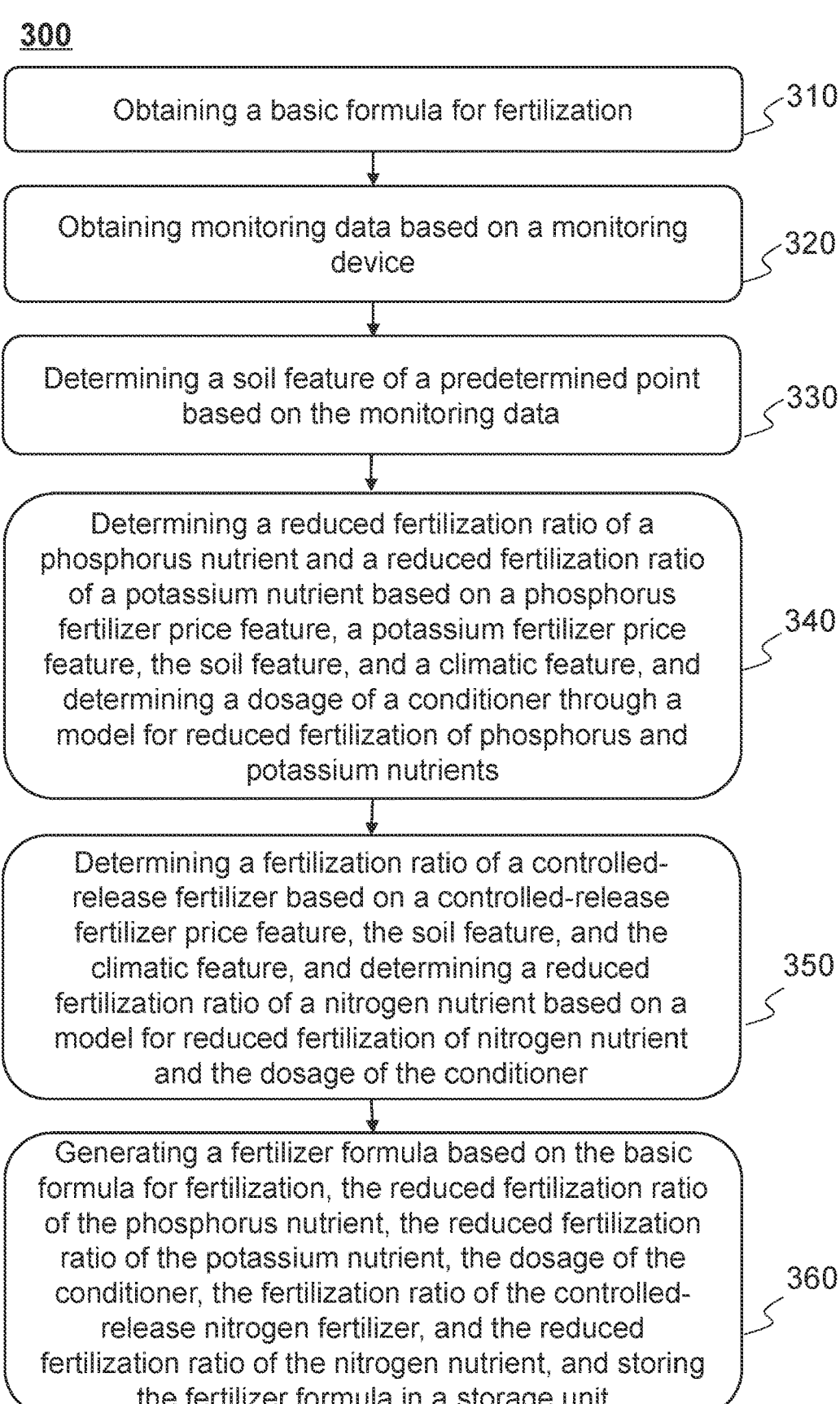

Obtaining a basic formula for fertilization    310

Obtaining monitoring data based on a monitoring device    320

Determining a soil feature of a predetermined point based on the monitoring data    330

Determining a reduced fertilization ratio of a phosphorus nutrient and a reduced fertilization ratio of a potassium nutrient based on a phosphorus fertilizer price feature, a potassium fertilizer price feature, the soil feature, and a climatic feature, and determining a dosage of a conditioner through a model for reduced fertilization of phosphorus and potassium nutrients    340

Determining a fertilization ratio of a controlled-release fertilizer based on a controlled-release fertilizer price feature, the soil feature, and the climatic feature, and determining a reduced fertilization ratio of a nitrogen nutrient based on a model for reduced fertilization of nitrogen nutrient and the dosage of the conditioner    350

Generating a fertilizer formula based on the basic formula for fertilization, the reduced fertilization ratio of the phosphorus nutrient, the reduced fertilization ratio of the potassium nutrient, the dosage of the conditioner, the fertilization ratio of the controlled-release nitrogen fertilizer, and the reduced fertilization ratio of the nitrogen nutrient, and storing the fertilizer formula in a storage unit    360

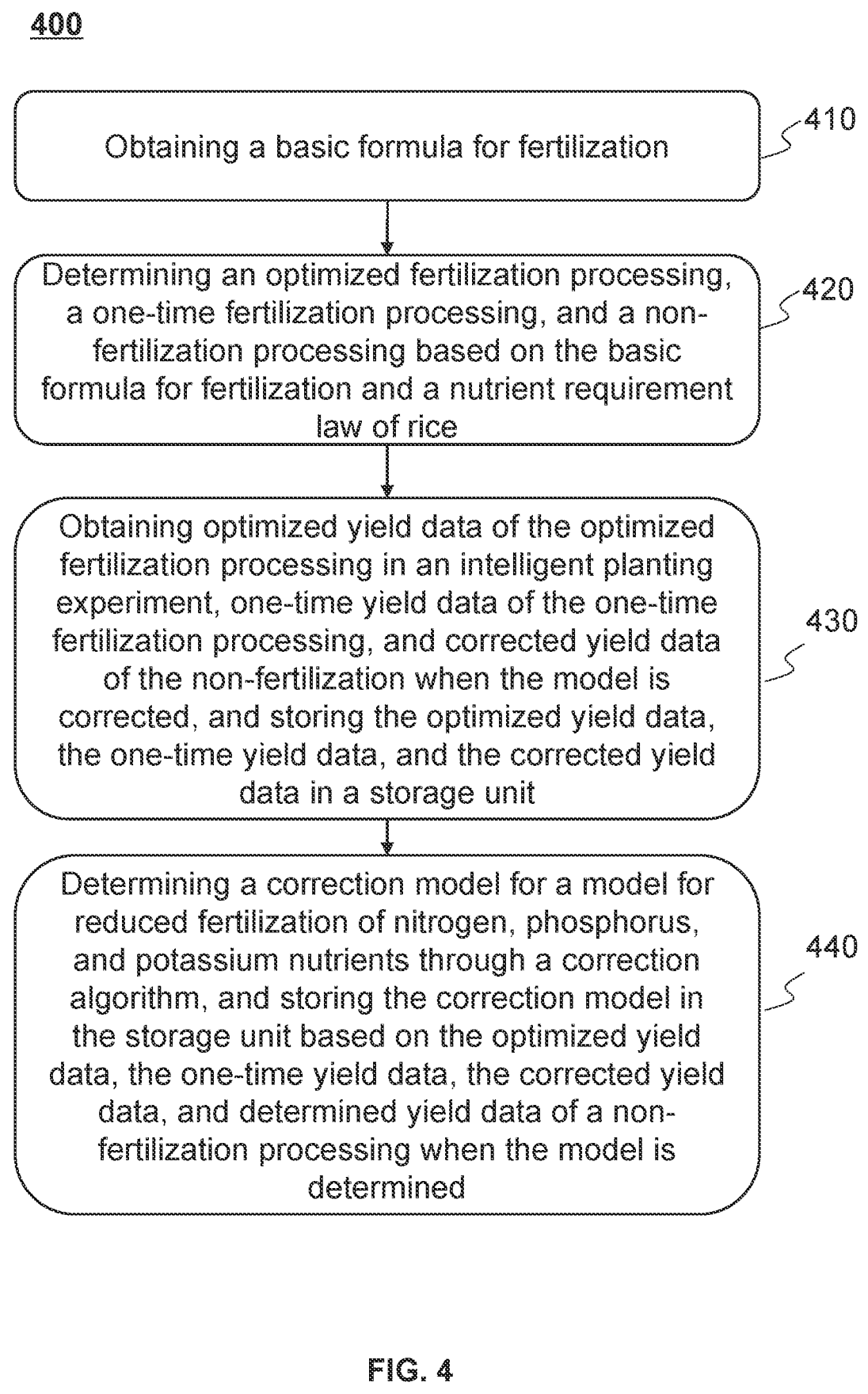

Obtaining a basic formula for fertilization — 410

Determining an optimized fertilization processing, a one-time fertilization processing, and a non-fertilization processing based on the basic formula for fertilization and a nutrient requirement law of rice — 420

Obtaining optimized yield data of the optimized fertilization processing in an intelligent planting experiment, one-time yield data of the one-time fertilization processing, and corrected yield data of the non-fertilization when the model is corrected, and storing the optimized yield data, the one-time yield data, and the corrected yield data in a storage unit — 430

Determining a correction model for a model for reduced fertilization of nitrogen, phosphorus, and potassium nutrients through a correction algorithm, and storing the correction model in the storage unit based on the optimized yield data, the one-time yield data, the corrected yield data, and determined yield data of a non-fertilization processing when the model is determined — 440

FIG. 4

METHODS AND SYSTEMS FOR GENERATING FERTILIZER FORMULAS

CROSS-REFERENCE TO RELATED APPLICATIONS

This application claims priority of Chinese Patent Application No. 2022111276151, filed on Sep. 16, 2022, the entire contents of which are incorporated herein by reference.

TECHNICAL FIELD

The present disclosure relates to the technical field of fertilization methods for plants, and in particular, to a method and a system for generating a fertilizer formula.

BACKGROUND

Rice is one of the important food crops in China, with a planting area of more than 400 million acres, accounting for about 30% of the area of food crops and about 50% of the total crop output. Currently, about two-thirds of the world's population relies on rice as a staple food. However, the rapid release of fertilizer nutrients and the short duration of fertilizer efficacy pose a challenge in meeting the nutritional demands of rice throughout its reproductive period. Consequently, the conventional method of multiple and large-scale fertilization results in a series of issues, including decreased rice quality, ecological pollution, exacerbated soil acidification, compromised biodiversity, and increased production costs. Therefore, the development of technologies related to fertilizer reduction and soil improvement has become an important approach for ensuring the safe production and promoting sustainable development of rice.

A controlled-release fertilizer and soil conditioner provide new ideas and ways to solve the problems of low utilization rate of fertilizers, declined soil quality, deteriorating rice quality, and environmental pollution. The controlled-release fertilizer increases the utilization rate of fertilizers and reduces the pollution to the environment by changing a release time of nutrients to enable the nutrients to be released when crops need fertilizers; the soil conditioner regulates soil acidity, improves soil structure, and increases the fertility of soil through the slow release of trace elements, the continuous decomposition of organic substances, and the continuous decomposition of microbial systems. The reasonable combination of the controlled-release fertilizer and soil conditioner and large-scale promotion in the long term will be able to achieve significant economic and social benefits. The existing controlled-release fertilizer technology focuses on solving the problem of one-time application of fertilizers and reduced fertilization of nitrogen fertilizer, and the conditioner mainly focuses on regulating undesirable traits of soil. However, research on how to reduce a dosage of nitrogen, phosphorus, potassium, and other elements when applying the soil conditioner is relatively limited, and research on how to optimize a reduced fertilization ratio of nitrogen, phosphorus, and potassium nutrients based on a combination of the controlled-release fertilizer with the soil conditioner are almost blank. Therefore, determining a scheme for reduced fertilization of nitrogen, phosphorus, and potassium nutrients according to a different proportion of the controlled-release fertilizer and an amount of the soil conditioner has become a major problem faced by fertilizer producers and planting households or cooperatives in the process of fertilizer application.

At present, a controlled-release fertilizer and soil conditioner for rice available in the market are pre-made products, making it difficult for rice farmers to customize the formula based on their specific conditions. Even though manufacturers provide dosage guidelines, it is challenging to achieve precise fertilizer reduction, considering the high cost of existing controlled-release fertilizers. This poses a significant burden for large-scale rice growers or cooperatives. If it is possible to effectively reduce the dosage of fertilizers according to a relevant model or method, and adjust a formula of fertilizers and a dosage of conditioner in real-time after buying raw materials, it can not only design formulations according to the local conditions to improve the utilization rate of fertilizers and improve the quality of soil, but also significantly reduce the input costs and environmental pollution.

SUMMARY

One or more embodiments of the present disclosure provide a method for generating a fertilizer formula, the method is performed by a processor, comprising: obtaining monitoring data based on a monitoring device, the monitoring device being deployed at a predetermined point of a target planting unit; determining a soil feature of the predetermined point based on the monitoring data; determining an experimental scheme and experimental parameters based on the soil feature and an experimental design, and the experimental scheme comprising one or more experimental processings and an optimized fertilization processing as a control, the experimental parameters comprising a dosage of a conditioner, a fertilization ratio of a controlled-release fertilizer, a reduced fertilization ratio of a nitrogen nutrient, a reduced fertilization ratio of a phosphorus nutrient, and a reduced fertilization ratio of a potassium nutrient; determining a fertilization dosage based on the experimental parameters and the basic formula for fertilization, and conducting an intelligent planting experiment based on the fertilization dosage and the experimental scheme; wherein the intelligent planting experiment comprises: obtaining a physicochemical feature at one or more time points corresponding to a predetermined sub-region of the target planting unit based on the monitoring device and compressing and storing the physicochemical feature within a predetermined compression intensity to obtain a physicochemical feature sequence of the predetermined sub-region, the physicochemical feature comprising at least one of a temperature, a humidity, a pH value, or an EC value, and the predetermined compression intensity being determined based on a residual storage capacity of a storage unit; determining whether an abnormal sub-region exists based on the physicochemical feature sequence; and in response to a determination that the abnormal sub-region exists, performing a predetermined processing on the abnormal sub-region; wherein the monitoring device collects the physicochemical feature at a first collection frequency and uploads the physicochemical feature to the processor, the first collection frequency is issued by the processor to the monitoring device within a first predetermined period, the first collection frequency is determined based on a free resource bandwidth of the processor in a future time period, and the first predetermined period is determined based on a change rate of a free resource bandwidth of the processor in a historical time period; obtaining experimental parameters and experimental yield data of each of the one or more experimental processings, and optimized yield data of the optimized fertilization processing, and storing the experimental parameters, the experimental yield data, and the optimized yield data in the storage unit; and determining a model for reduced fertilization of nitrogen, phosphorus, and potassium nutrients based the experimental parameters, the experimental yield data, and the optimized yield data through a regression model, and storing the model for reduced fertilization of nitrogen, phosphorus, and potassium nutrients in the storage unit, wherein the regression model is extracted by the processor from the storage unit, and the model for reduced fertilization of nitrogen, phosphorus, and potassium nutrients comprises a model for reduced fertilization of phosphorus and potassium nutrients and a model for reduced fertilization of nitrogen nutrient.

One or more embodiments of the present disclosure provide a system for generating a fertilizer formula, comprising a processor, the processor being configured to perform the aforementioned method for generating a fertilizer formula.

One or more embodiments of the present disclosure provide a method for generating a fertilizer formula, and the method is performed by a processor, comprising: obtaining a basic formula for fertilization; obtaining monitoring data based on a monitoring device, the monitoring device being deployed at a predetermined point of a target planting unit; determining a soil feature of the predetermined point based on the monitoring data; determining a reduced fertilization ratio of a phosphorus nutrient and a reduced fertilization ratio of a potassium nutrient based on a phosphorus fertilizer price feature, a potassium fertilizer price feature, a soil feature, and a climate feature, and determine a dosage of a conditioner by means of a model for reduced fertilization of phosphorus and potassium nutrients, wherein the phosphorus fertilizer price feature, the potassium fertilizer price feature, the soil feature, and the climate feature are obtained by the processor from one or more Internet of Things units, and the processor is connected to the Internet of Things units in communication connection; determining a fertilization ratio of a controlled-release fertilizer based on a controlled-release fertilizer price feature, the soil feature, and the climate feature, and determining a reduced fertilization ratio of a nitrogen nutrient by means of a model for reduced fertilization of nitrogen nutrient and the dosage of the conditioner; and determining the fertilization formula based on the basic formula for fertilization, the reduced fertilization ratio of the phosphorus nutrient, the reduced fertilization ratio of the potassium nutrient, the dosage of the conditioner, a fertilization ratio of a controlled-release nitrogen fertilizer, and the reduced fertilization ratio of the nitrogen nutrient, and storing the fertilization formula in a storage unit; the model for reduced fertilization of phosphorus and potassium nutrients and the model for reduced fertilization of nitrogen nutrient being obtained by the method for generating a fertilizer formula.

One or more embodiments of the present disclosure provide a system for generating a fertilizer formula, comprising a processor, the processor being configured to perform the aforementioned method for generating a fertilizer formula.

One or more embodiments of the present disclosure provide a method for correcting a model for reduced fertilization of nitrogen, phosphorus and potassium nutrients, the model for reduced fertilization of nitrogen, phosphorus and potassium nutrients being obtained by the above mentioned method for generating a fertilizer formula, and the method is executed by a processor, comprising: obtaining a basic formula for fertilization; determining an optimized fertilization processing, a one-time fertilization processing and non-fertilization processing based on the basic formula for fertilization and a nutrient requirement law of rice, wherein the nutrient requirement law of rice is pre-stored in a storage unit; obtaining optimized yield data of the optimized fertilization processing, one-time yield data of the one-time fertilization processing, and corrected yield data of the non-fertilization processing when the model is corrected in an intelligent planting experiment, and storing the optimized yield data, the one-time yield data, and the corrected yield data in the storage unit; wherein the intelligent planting experiment comprises: obtaining, based on a monitoring device, physicochemical features of a predetermined sub-region of a target planting unit at one or more time points, and compressing and storing the physicochemical features within a predetermined compression intensity to obtain a physicochemical feature sequence of the predetermined sub-region, the physicochemical features comprising at least one of a temperature, a humidity, a pH value, or an EC value, the predetermined compression intensity being determined based on a remaining storage capacity of the storage unit; based on the physicochemical feature sequence, determining whether an abnormal sub-region exists; in response to a determination that the abnormal sub-region exists, performing a predetermined processing on the abnormal sub-region; wherein the monitoring device collects the physicochemical feature at a first collection frequency and uploads the physicochemical feature to the processor, the first collection frequency is issued by the processor to the monitoring device within a first predetermined period, the first collection frequency is determined based on a free resource bandwidth of the processor in a future time period, and the first predetermined period is determined based on a change rate of a free resource bandwidth of the processor in a historical time period; and based on the optimized yield data, the one-time yield data, the corrected yield data, and determined yield data of the non-fertilization processing when the model is determined, determining a correction model for the model for reduced fertilization of nitrogen, phosphorus, and potassium nutrients using a correction algorithm, and storing the correction model in the storage unit, wherein the correction algorithm is pre-stored in the storage unit.

One or more embodiments of the present disclosure provide a system for correcting a model for reduced fertilization of nitrogen, phosphorus, and potassium nutrients, comprising a processor, the processor being configured to perform the aforementioned method for correcting a model for reduced fertilization of nitrogen, phosphorus, and potassium nutrients.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering denotes the same structure, wherein:

FIG. 1 is a flowchart illustrating an exemplary method for generating a fertilizer formula according to some embodiments of the present disclosure;

FIG. 3 is a flowchart illustrating another exemplary method for generating a fertilizer formula according to some embodiments of the present disclosure; and FIG. 4 is a flowchart illustrating an exemplary method for correcting a model for reduced fertilization of nitrogen, phosphorus, and potassium nutrients according to some embodiments of the present disclosure.

DETAILED DESCRIPTION

Figure 2:
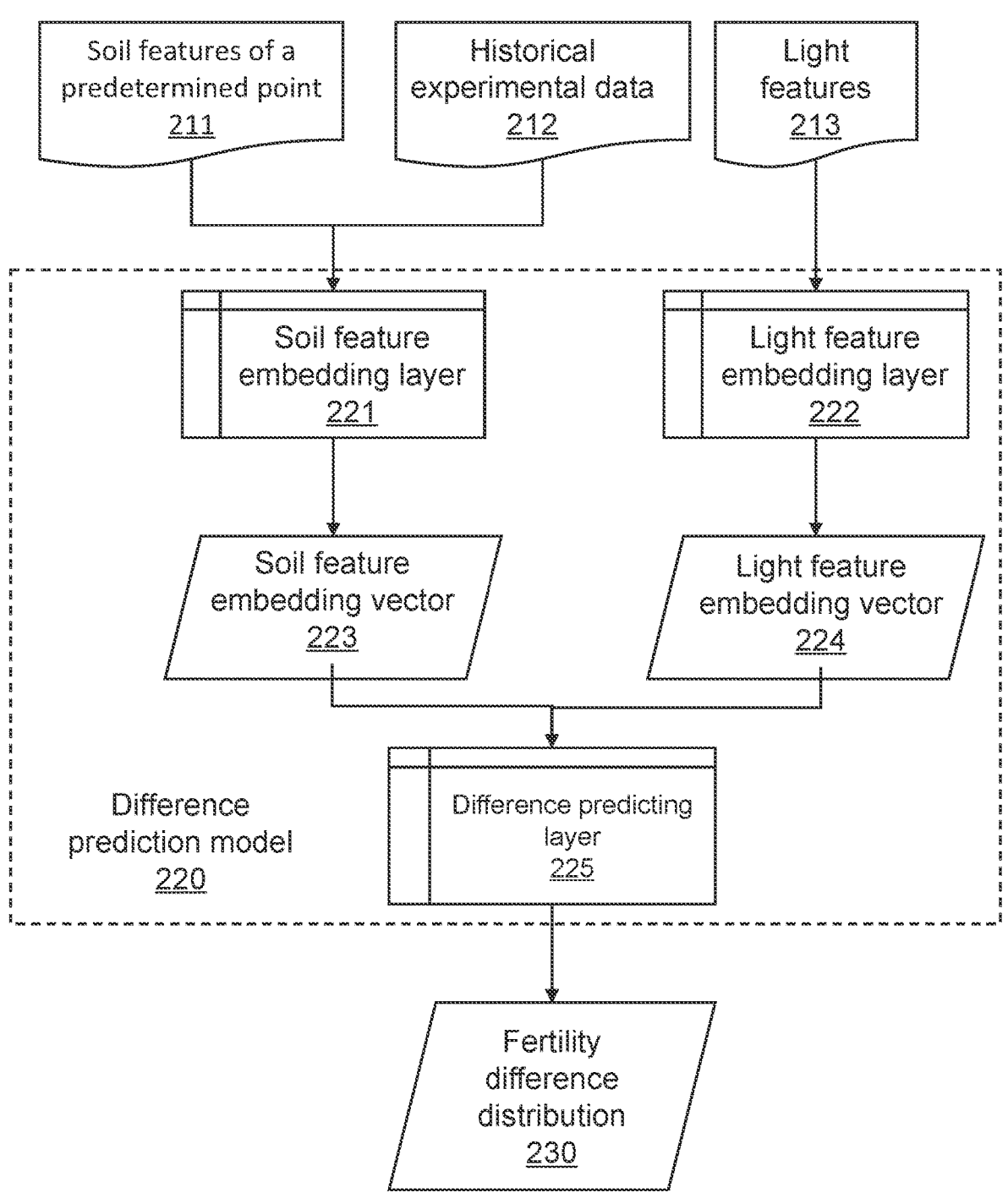
FIG. 2 is a schematic diagram illustrating an exemplary difference prediction model according to some embodiments of the present disclosure.

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with these drawings without creative labor. The present disclosure can be applied to other similar scenarios based on these drawings without the expenditure of creative labor. Unless obviously obtained from the context or the context illustrates otherwise, the same numeral in the drawings refers to the same structure or operation.

It should be understood that the terms "system", "device", "unit" and/or "module" as used herein is a way to distinguish between different components, elements, parts, sections, or assemblies at different levels. However, the words may be replaced by other expressions if other words accomplish the same purpose.

As shown in the present disclosure and the claims, unless the context clearly suggests an exception, the words "one," "a", "one kind" and/or "the" do not refer specifically to the singular, but may also include the plural. Generally, the terms "including" and "comprising" suggest only the inclusion of clearly identified steps and elements, but the steps and elements do not constitute an exclusive list, and the method or device may also include other steps or elements.

Flowcharts are used in the present disclosure to illustrate operations performed by a system according to embodiments of the present disclosure. It should be appreciated that the preceding or following operations are not necessarily performed in an exact sequence. Instead, steps can be processed in reverse order or simultaneously. Also, it is possible to add other operations to these processes, or to remove a step or steps from these processes.

FIG. 1 is a flowchart illustrating an exemplary method for generating a fertilizer formula according to some embodiments of the present disclosure. In some embodiments, a process 100 may be executed by a processor. As shown in FIG. 1, the process 100 includes following steps.

Step 110, obtaining a basic formula for fertilization.

The basic formula for fertilization is a common formula for fertilization corresponding to a crop. For example, the basic formula for fertilization may include a requirement for each nutrient element, such as nitrogen, phosphorus, potassium, etc., per unit area of the crop.

In some embodiments, when the crop is rice, the basic formula for fertilization is associated with a specific type of rice. The type of rice includes early rice, middle rice, and late rice.

For example, a basic formula for fertilization for the early rice is a fertilization dosage of pure nitrogen (N) is 10-15 kg/mu (which is a Chinese unit of area, and 1 mu equals about 0.16 acres), a fertilization dosage of pure phosphorus $(P_2O_5)$ is 5-8 kg/mu, and a fertilization dosage of pure potassium $(K_2O)$ is 8-12 kg/mu, wherein a controlled-release period of a controlled-release nitrogen fertilizer for the early rice is 50-75 days. As another example, a basic formula for fertilization for the middle rice or the late rice is a fertilization dosage of pure nitrogen (N) is 12-18 kg/mu, a fertilization dosage of pure phosphorus $(P_2O_5)$ is 5-8 kg/mu, and a fertilization dosage of pure potassium $(K_2O)$ is 8-12 kg/mu, wherein a controlled-release period of a controlled-release nitrogen fertilizer for the late rice is 70-105 days.

In some embodiments, the basic formula for fertilization for the early rice may include N: 12 kg/mu; $P_2O_5$:6 kg/mu; and $K_2O$: 10 kg/mu, and the basic formula for fertilization for the late rice may include N: 14 kg/mu; $P_2O_5$:6 kg/mu; and $K_2O$: 10 kg/mu. A variety of the early rice may include Xinrongyou No. 5, and a variety of the late rice may include Wuyou Huazhan.

In some embodiments, an experimental site may be set up in any field where an experiment may be conducted, e.g., Fenglong Village, HeShi Town, Taihe County, Jiangxi Province.

In some embodiments, the processor may apply any conditioners, conventional nitrogen fertilizers, controlled-release nitrogen fertilizers, phosphorus fertilizers, potassium fertilizers, or the like that may be used to conduct the experiment, such as a silica-calcium-potassium-magnesium fertilizer, urea, and resin-coated urea produced by Jinzhengda Eco-Engineering Group Co. Ltd, a phosphorus fertilizer produced by Yunnan Yuntianhua Co. Ltd, a potassium fertilizer produced by Sinochem Corporation, etc., which is not limited in the present disclosure.

In some embodiments, a soil conditioner may be selected from a silica-calcium-potassium-magnesium fertilizer that complies with a national standard (GBT 36207 2018), a conditioner product produced in accordance with an invention patent (ZL201510556136.5) or a soil conditioner product containing calcium, magnesium, phosphorus, potassium, silicon, and other nutrients. This is because soil conditioner product containing calcium, magnesium, phosphorus, potassium, silicon, and other nutrients can not only effectively supplement trace elements in soil, significantly improve soil acidity, but also significantly reduce the dosage of nitrogen fertilizer by producing an interactive effect with the controlled-release nitrogen fertilizer when the dosage of the soil conditioner product is greater than 50 kg/mu.

In some embodiments, the processor may access relevant information pre-stored in the storage unit to determine the basic formula for fertilization. The relevant information may include literature, technical specifications, or historical data. In some embodiments, the fertilizer base formula may be obtained based on the Technical Specification for Soil Formula Fertilizer Measurement (Revised 2011) (hereinafter referred to as the Specification).

Step 120, obtaining monitoring data based on a monitoring device, the monitoring device being deployed at a predetermined point of a target planting unit.

The predetermined point may be set in advance based on actual needs. For example, the processor may divide the target planting unit into one or more regions equally, and determine a center of each region as a predetermined point.

The monitoring device refers to a device for obtaining the monitoring data. In some embodiments, the monitoring device may include a sensor, e.g., a temperature sensor, a humidity sensor, a pH sensor, an EC value, etc.

The monitoring data refers to soil-related data, for example, a temperature, humidity, pH value, conductivity of soil, etc.

The target planting unit is a field selected for an intelligent planting experiment that is available for a planting experiment. In some embodiments, one or more predetermined points may be set up in the target planting unit to place more monitoring devices to obtain more comprehensive monitoring data.

Step 130, determining a soil feature of the predetermined point based on the monitoring data.

The soil feature is a feature related to soil properties, such as a temperature, humidity, pH value, EC value, porosity, water content, oxygen content, and distribution of elemental contents (e.g., elements such as P, N, C, O).

In some embodiments, the monitoring data may be used directly as the soil feature. In some embodiments, the processor may directly determine the soil feature of the predetermined point through the monitoring data obtained by the monitoring device, for example, the temperature, humidity, pH value, EC value, or the like of the soil.

In some embodiments, the processor may collect a soil sample via a sampling device, conduct a laboratory test on the soil sample, and then determine the soil feature (e.g., the porosity, water content, oxygen content, distribution of elemental contents, or the like) of the predetermined point based on a result of the laboratory test.

Step 140, determining an experimental scheme and experimental parameters based on the soil feature and an experimental design.

The experimental scheme is a fertilization scheme for conducting the intelligent planting experiment.

In some embodiments, the processor may determine the experimental scheme based on an experimental factor and an experimental level through an experimental design, wherein the experimental design may include a uniform experimental design and an orthogonal experimental design.

The experimental factor is a variable factor to be treated in the experimental scheme. For example, the experimental factor may include the conditioner, the phosphorus nutrient, the nitrogen nutrient, etc.

The experimental level is a level or state corresponding to the experimental factor. For example, the experimental level may include a dosage of the conditioner, a reduced fertilization ratio of the phosphorus nutrient, and a reduced fertilization ratio of the nitrogen nutrient, or the like.

In some embodiments, the experimental scheme may include one or more experimental processings and an optimized fertilization processing as a control.

In some embodiments, the process may determine the one or more experimental processings based on the uniform experimental design or the orthogonal experimental design. For example, the processor may preset experimental factors and a plurality of experimental levels corresponding to each of the experimental factors and combine the plurality of experimental levels corresponding to the each of the experimental factors though the uniform experimental design or the orthogonal experimental design to determine the one or more experimental processings.

The experimental parameters refer to an experimental level corresponding to each experimental factor of each experimental processing in the experimental scheme. The experimental parameters include the dosage of the conditioner, a fertilization ratio of a controlled-release fertilizer, and a reduced fertilization ratio of a nutrient, wherein the reduced fertilization ratio of the nutrient includes the reduced fertilization ratio of the nitrogen nutrient, the reduced fertilization ratio of the phosphorus nutrient, and a reduced fertilization ratio of the potassium nutrient. In some embodiments, the fertilization ratio of the controlled-release fertilizer may include a fertilization ratio of the controlled-release nitrogen fertilizer.

The fertilization ratio of the controlled-release fertilizer refers to a proportion of different nutrients in the controlled-release fertilizer. In some embodiments, the fertilization ratio of the controlled-release fertilizer may be a mass ratio or a volume ratio, e.g., if nitrogen is required for a certain crop, and every 100 kilograms of the controlled-release fertilizer contains 15 kilograms of nitrogen, a fertilization ratio of the controlled-release nitrogen fertilizer should be 100:15.

The reduced fertilization ratio of the nutrient is a ratio of a dosage of a nutrient that may be reduced after using the controlled-release fertilizer to a dosage of a nutrient used in conventional fertilization. For example, if a dosage of the nitrogen fertilizer may be reduced by 30% after using the controlled-release fertilizer, then the reduced fertilization ratio of the nitrogen nutrient is 0.3.

The optimized fertilization processing refers to fertilizing a reasonable proportion of various nutrients according to factors such as crop species, growth stage, and soil conditions during a process of fertilization to achieve the best fertilization effect.

In some embodiments, the processor may determine the optimized fertilization processing based on an experimental parameter of a normal dosage level, wherein the normal dosage level may be consistent with a dosage level corresponding to an experimental factor of the basic formula for fertilization.

In some embodiments, the processor may determine a historical optimized experimental processing in historical data as the optimized fertilization processing. In some embodiments, the processor may query a table of experimental processings to determine the optimized fertilization processing based on the soil feature, wherein the table of experimental processings store different sets of soil feature data and historical optimized fertilization processings corresponding to the sets of soil feature data. The table of experimental processings may be obtained based on experience or historical data.

In some embodiments, the processor may also determine the optimized fertilization processing based on the soil feature by means of vector retrieval. For example, the processor may construct a to-be-matched vector based on the soil feature, and the processor may retrieve in a vector database based on the to-be-matched vector to obtain a reference vector whose vector distance with the to-be-matched vector satisfies a distance condition, and determine a historical optimized fertilization processing corresponding to the reference vector as the optimized fertilization processing. The vector database is used to store a plurality of historical vectors and historical optimized fertilization processings corresponding to the plurality of historical vectors, wherein the historical vector is constructed based on a historical soil feature.

In some embodiments, the optimized fertilization processing determined by the processor may be using soil testing formula fertilizing technology for fertilization; wherein the nitrogen fertilizer is used in three times as a base fertilizer, a tiller fertilizer, and a spike fertilizer, respectively, and the phosphorus fertilizer and the potassium fertilizer are used all at once.

In some embodiments, the processor may determine the experimental scheme in a variety of ways, e.g., the processor may determine the experimental scheme based on the experimental level by a uniform experimental design or an orthogonal experimental design.

In some embodiments, without reducing the nitrogen nutrient and without fertilizing the controlled-release nitrogen fertilizer, the processor may use the conditioner, the phosphorus nutrient, and the potassium nutrient as three experimental factors, and use the dosage of the conditioner, the reduced fertilization ratio of the phosphorus nutrient, and the reduced fertilization ratio of the potassium nutrient as three experimental levels, and use the uniform experimental design to obtain a first experimental scheme.

The processor may determine the experimental parameters based on a preset range of experimental parameters. In some embodiments, the processor may set a series of dosage levels in accordance with an arithmetic sequence within a dosage range of the conditioner based on the uniform experimental design, and set a series of reduced fertilization ratios in accordance with an arithmetic sequence within a reduced fertilization ratio range of the phosphorus nutrient and a reduced fertilization ratio range of the potassium nutrient based on the uniform experimental design, wherein the dosage range of the conditioner is 0-250 kg/mu, and the reduced fertilization ratio range of the phosphorus nutrient and potassium nutrient is 0-65% and 0-50%, respectively.

For example, the processor may set the dosage of the conditioner at eight dosage levels, such as 0, 30, 60, 90, 120, 150, 180, and 210 kg/mu, set the reduced fertilization ratio of the phosphorus nutrient at eight reduced fertilization ratio levels such as 0%, 9%, 18%, 27%, 36%, 45%, 54%, and 63%, and set the reduced fertilization ratio of the potassium nutrient at eight reduced fertilization ratio levels such as 0%, 7%, 14%, 21%, 28%, 35%, 42%, and 49% in accordance with a $U8(8^3)$ uniform experimental design and the arithmetic sequence. According to a U8 $(8^3)$ uniform experimental design table, the first experimental scheme is obtained, and the optimized fertilization processing was designed that no conditioner is used and a dosage level of the phosphorus nutrient and potassium nutrient is normal.

In some embodiments, without reducing the phosphorus nutrient and the potassium nutrient, the processor may also use the conditioner, the controlled-release nitrogen fertilizer, and the nitrogen nutrient as three experimental factors, and use the dosage of conditioner, the fertilization ratio of the controlled-release nitrogen fertilizer, and the reduced fertilization ratio of the nitrogen nutrient as three experimental levels, and obtain a second experimental scheme using a"3414" orthogonal experimental design.

In some embodiments, the processor may set a series of dosage levels within the dosage range of the conditioner according to the "3414" experimental design and the arithmetic sequence, set a series of fertilization ratios within the fertilization ratio range of the controlled-release nitrogen fertilizer, and set a series of reduced fertilization ratios of the nitrogen nutrient according to the "3414" experimental design and the arithmetic sequence, wherein the dosage level of the conditioner is 0-250 kg/mu, the fertilization ratio of the controlled-release nitrogen fertilizer is 0%-85%, and the reduced fertilization ratio of the nitrogen nutrient is 0%-50%.

For example, the processor may set the dosage level of the conditioner at 4 levels such as 0, 50, 100, and 150 kg/mu, set the fertilization ratio of the controlled-release nitrogen fertilizer at 4 levels such as 0%, 25%, 50%, and 75%, and set the reduced fertilization ratio of the nitrogen nutrient at 4 levels such as 0%, 15%, 30%, and 45% in accordance with the "3414" experimental design and the arithmetic sequence. According to a "3414" orthogonal experimental design table, the second experimental scheme is obtained, and the optimized fertilization processing was designed that no controlled-release fertilizer is used and a dosage of the nitrogen nutrient is normal.

In some embodiments, the processor determines first preferred experimental level sets corresponding to the dosage of the conditioner, the reduced fertilization ratio of the phosphorus nutrient, and the reduced fertilization ratio of the potassium nutrient, respectively, based on the soil feature of the predetermined point; and determine the first experimental scheme using the uniform experimental design based on the first preferred experimental level sets.

In some embodiments, the processor determines second preferred experimental level sets corresponding to the dosage of the conditioner, the fertilization ratio of the phosphorus nutrient, and the reduced fertilization ratio of the nitrogen nutrient respectively based on the soil feature of the predetermined point; and determine the second experimental scheme using the orthogonal experimental design based on the second preferred experimental level sets.

The preferred experimental level set is a collection of experimental levels that may be more appropriate for the target planting unit. For example, the preferred experimental level set may include a preferred experimental level set for the dosage of the conditioner, a preferred experimental level set for the reduced fertilization ratio of the potassium nutrient, a preferred experimental level set for the fertilization ratio of the controlled-release nitrogen fertilizer, etc.

In some embodiments, the processor may determine the first preferred experimental level sets corresponding to the dosage of the conditioner, the reduced fertilization ratio of the phosphorus nutrient, and the reduced fertilization ratio of the potassium nutrient, respectively, by querying a first preset table of experimental levels and a first vector database of experimental levels. A plurality of sets of soil features and a plurality of preferred experimental level sets corresponding to the plurality of sets of soil features are stored in the first preset table of experimental levels and the first vector database of experimental levels.

In some embodiments, the processor may determine the second preferred experimental level sets corresponding to the dosage of the conditioner, the fertilization ratio of the phosphorus nutrient, and the reduced fertilization ratio of the nitrogen nutrient, respectively, by querying the first preset table of experimental levels and the first vector database of experimental levels.

In some embodiments, the first preset table of experimental levels or the first vector database of experimental levels may be determined based on historical data. For example, the processor may obtain a guidance accuracy and ubiquity of a model for reduced fertilization of nitrogen, phosphorus, and potassium nutrients obtained from the intelligent planting experiment of the experimental scheme, determine an experimental scheme whose guidance accuracy is greater than an accuracy threshold and ubiquity is greater than a ubiquity threshold, and determine a soil feature and experimental level set corresponding to a determined experimental scheme as a record in the first preset table of experimental levels or the first vector database of experimental levels.

The guidance accuracy refers to a conformity degree between a reduced dosage of nitrogen, phosphorus, and potassium nutrients for fertilization calculated by the model for reduced fertilization of nitrogen, phosphorus, and potassium nutrients and an expectedly reduced dosage of nitrogen, phosphorus, and potassium nutrients for fertilization in reality. In some embodiments, after applying the model for reduced fertilization of nitrogen, phosphorus, and potassium nutrients obtained from the intelligent planting experiment to a plurality of actual production environments, the processor may determine a ratio between a count of actual production environments that have a better application effect and a total count of actual production environments as the guidance accuracy. The better application effect may include: a utilization rate of a fertilizer is greater than a utilization rate threshold, an environmental impact level is less than a pollution threshold, and/or a cost of a fertilizer is less than a cost threshold.

The ubiquity is an applicable degree of the model for reduced fertilization of nitrogen, phosphorus, and potassium nutrients in different environments. In some embodiments, after applying the model for reduced fertilization of nitrogen, phosphorus, and potassium nutrients obtained from the intelligent planting experiment to a plurality of different actual scenarios (e.g., regions with different climates, regions with different altitudes, or the like), the processor may determine a ratio between a count of scenarios that have a better application effect and a total count of actual scenarios as the ubiquity.

In some embodiments, the processor determines a fertility difference distribution of the target planting unit based on a soil feature of the predetermined point at one or more time points, the fertility difference distribution including a difference value of soil fertility between predetermined subregions within the target planting unit; and determine the first preferred experimental level sets and the second preferred experimental level sets corresponding to the dosage of the conditioner, the reduced fertilization ratio of the phosphorus nutrient, and the reduced fertilization ratio of the potassium nutrient respectively based on the soil feature of the predetermined point at the one or more time points and the fertility difference distribution.

The one or more time points refer to one or more points within a preset time range prior to conducting the intelligent planting experiment. The preset time range may be set based on experience or actual needs.

The soil fertility refers to the ability of soil to provide a nutrient for plant growth. In some embodiments, the processor may determine the soil fertility via the monitoring device deployed at the predetermined point of the target planting unit.

The fertility difference distribution refers to a distribution feature of soil fertility in the target planting unit. In some embodiments, the fertility difference distribution includes the difference value of soil fertility between predetermined sub-regions within the target planting unit.

In some embodiments, the processor may determine the fertility difference distribution in the target planting unit by querying a preset table of fertility distribution based on the soil feature of the predetermined point at the one or more time points. A plurality of sets of soil features and a plurality of fertility difference distributions corresponding to the plurality of sets of soil features are stored in the preset table of fertility distribution.

In some embodiments, the processor may also determine the fertility difference distribution based on the soil feature of the predetermined point at the one or more time points by means of a difference prediction model. Please refer to FIG. 2 and its related descriptions for a more detailed description of the difference prediction model.

In some embodiments, the processor may determine the first preferred experimental level sets and/or the second preferred experimental level sets by querying a second preset table of experimental levels or a second vector database of experimental levels based on the soil feature and the fertility difference distribution of the predetermined point. The second preset table of experimental levels and the second vector database of experimental levels store a plurality of sets of soil features and fertility difference distributions and a plurality of preferred experimental level sets corresponding the plurality of sets of soil features and fertility difference distributions. The second preset table of experimental levels or the second vector database of experimental levels is constructed in a manner similar to the manner in which the first preset table of experimental levels or the first vector database of experimental levels is constructed and may be referred to in the relevant description above.

In some embodiments of the present disclosure, based on the soil feature and the fertility difference distribution of the predetermined point, it helps to determine a preferred experimental level set that is more in line with the physicochemical properties of the soil of the target planting unit, and to reduce errors in a subsequent intelligent planting experiment due to the soil fertility difference, so as to obtain a more accurate model for reduced fertilization of nitrogen, phosphorus, and potassium nutrients.

In some embodiments, without reducing the nitrogen nutrient and without fertilizing the controlled-release nitrogen fertilizer, the processor may use the conditioner, the phosphorus nutrient, and the potassium nutrient as three experimental factors, and obtain a first experimental scheme using the uniform experimental design based on the first preferred experimental level sets corresponding to the dosage of the conditioner, the reduced fertilization ratio of the phosphorus nutrient, and the reduced fertilization ratio of the potassium nutrient.

In some embodiments, the processor may determine the second preferred experimental level sets corresponding to the dosage of the conditioner, the fertilization ratio of the controlled-release nitrogen fertilizer, and the reduced fertilization ratio of the nitrogen nutrient respectively by querying the first or second preset table of experimental levels or the first or second vector database of experimental levels based on the soil feature and/or the fertility difference distribution of the predetermined point.

In some embodiments, without applying the phosphorus nutrient and potassium nutrient, the processor may use the conditioner, the controlled-release nitrogen fertilizer, and the nitrogen nutrient as three experimental factors, and determine a second experimental scheme using the "3414", L16 ($4^3$), or L25 ($5^3$) orthogonal experimental design based on the second preferred experimental level sets corresponding to the dosage of the conditioner, the fertilization ratio of the controlled-release nitrogen fertilizer, and the reduced fertilization ratio of the nitrogen nutrient.

In some embodiments of the present disclosure, based on the soil feature of the predetermined point, it helps to determine a preferred experimental level set that is more in line with the physicochemical properties of the soil of the target planting unit, and to reduce errors in a subsequent intelligent planting experiment due to different physicochemical properties of the soil, so as to obtain a more accurate model for reduced fertilization of nitrogen, phosphorus, and potassium nutrients.

Step 150, determining a fertilization dosage based on the experimental parameters and the basic formula for fertilization, and conducting an intelligent planting experiment based on the fertilization dosage and the experimental scheme.

In some embodiments, the processor may determine the dosage of the conditioner, a dosage of the controlled-release fertilizer, a dosage of the nitrogen nutrient, a dosage of the phosphorus nutrient, and a dosage of the potassium nutrient based on the experimental parameters and the basic formula for fertilization, thereby determining the fertilization dosage.

In some embodiments, the process may perform a fertilization processing on the target planting unit based on a determined fertilization dosage and the experimental scheme and plant crops to conduct the intelligent planting experiment.

In some embodiments, the intelligent planting experiment comprises:

Step 151, obtaining a physicochemical feature at one or more time points corresponding to a predetermined sub-region of the target planting unit based on the monitoring device and compressing and storing the physicochemical feature within a predetermined compression intensity to obtain a physicochemical feature sequence of the predetermined sub-region.

The predetermined sub-region is a region in which one experimental scheme is conducted separately, for example, according to each 5 m×5 m square area, an experimental field of 30 m×30 m may be divided into 36 independent spaces and each of which could be used for a separate experimental processing. In some embodiments, the same experimental processing may be repeated multiple times in each predetermined sub-region.

The physicochemical feature is a physical and chemical feature of soil within the predetermined sub-region. For example, the physicochemical feature may include at least one of a temperature, humidity, pH value, or EC value of the soil.

Compression is a technique of processing data to reduce an amount of data, e.g., 5 numbers: 3.01, 3.02, 3.01, 2.99, and 2.97, may be compressed into "3, and 0.02". That is, a set of numbers is represented by a statistical feature (e.g., mean+standard deviation), thus achieving the purpose of compression.

The predetermined compression intensity may be used to measure an intensity of compression. In some embodiments, every N numbers (e.g., N=5 as mentioned in the previous example) may be compressed once as described, wherein N is the predetermined compression intensity.

In some embodiments, the greater the predetermined compression intensity, the greater the intensity of compression and the smaller the space occupied by data after compression.

In some embodiments, the predetermined compression intensity may be determined based on a variety of ways, for example, a remaining storage capacity of the storage unit, a progress requirement for the physicochemical feature, or the like. In some embodiments, the greater the remaining storage capacity of the storage unit, the lower the predetermined compression intensity may be.

In some embodiments, the processor may periodically clear a space within the storage unit, e.g., it may only retain data of the most recent m days, i.e., it may empty the data within the storage unit every m days.

The physicochemical feature sequence is a series of physicochemical features at a plurality of time points based on a chronological order.

In some embodiments, the processor may obtain physicochemical features at the one or more time points corresponding to the predetermined sub-region obtained by the monitoring device, arrange the physicochemical features at the one or more time points based on an order of obtaining time, and compress and store the physicochemical features within the predetermined compression intensity to obtain the physicochemical feature sequence of the predetermined sub-region.

Step 152, determining whether an abnormal sub-region exists based on the physicochemical feature sequence.

The abnormal sub-region is a predetermined sub-region whose physicochemical feature does not meet a predetermined requirement.

In some embodiments, the processor may determine whether the abnormal sub-region exists based on a plurality of physicochemical feature sequences obtained by a plurality of repetitive experiments in each predetermined sub-region by determining whether the plurality of physicochemical feature sequences meets the predetermined requirement. For example, a failure to meet the predetermined requirement may include that a difference value between two physicochemical feature sequences is greater than a predetermined difference threshold, and a count of difference values in which the difference value between two physicochemical feature sequences is greater than the predetermined difference threshold is greater than a predetermined count.

In some embodiments, each predetermined sub-region conducts K repetitive experiments based on the same experimental scheme, and the processor may calculate K physicochemical feature sequences corresponding to the K repetitive experiments and a difference value between every two physicochemical feature sequences, and if a plurality of difference values of the predetermined sub-region does not meet the predetermined requirement, then the predetermined sub-region is determined as the abnormal sub-region.

Exemplarily, a predetermined sub-region area1 is subjected to 3 repetitive experiments, and the processor collects physicochemical features at a plurality of time points during each experiment to constitute a physicochemical feature sequence, which in turn determines that the 3 repetitive experiments correspond to 3 physicochemical feature sequences a1, a2, and a3. A difference value d1 between a1 and a2 is calculated, a difference value d2 between a1 and a3 is calculated, and a difference value d3 between a2 and a3 is calculated, and the predetermined sub-region area1 is determined as the abnormal sub-region if two of d1, d2, and d3 are greater than a predetermined threshold.

In some embodiments, the processor may calculate a difference value between each set of corresponding elements in the two physicochemical feature sequences, and determine an average value of a plurality of difference values as the difference value. Exemplarily, if two physicochemical feature sequences are a1 and a2, respectively, including an element a11 and an element a21 respectively, wherein an obtaining time of the element a11 from an initial obtaining time in the physicochemical feature sequence a1 is t1, and an obtaining time of the element a21 from an initial obtaining time in the physiochemical feature sequence a2 is t1, then the element a11 and element a21 are a set of corresponding elements.

Step 153, in response to a determination that the abnormal sub-region exists, performing a predetermined processing on the abnormal sub-region.

In some embodiments, in response to the abnormal sub-region exists, the processor may perform one or more predetermined processings on the abnormal sub-region. The predetermined processing includes at least three of the following:

(1) discarding data related to all experimental schemes corresponding to the abnormal sub-region and not using the data as data for subsequent regression analysis.

(2) with respect to a certain experimental processing in the abnormal sub-region, obtaining a plurality of physicochemical feature sequences based on multiple repetitive experiments of the experimental scheme, and determining a certain repetitive experiment that has abnormal data based on a difference value between a plurality of sets of physicochemical feature sequences and discarding data related to the repetitive experiment and not using the data for the subsequent regression analysis. For example, if a difference value d1 between a1 and a2 is greater than the predetermined threshold, a difference value d2 between a1 and a3 is greater than the predetermined threshold, and a difference value d3 between a2 and a3 is located in a normal range, it is possible that an environmental feature of repetitive experiments corresponding to a1 deviates seriously, and environments of repetitive experiments corresponding to a2 and a3 are normal, then data of the repetitive experiments corresponding to a1 is discarded, and data of the repetitive experiments corresponding to a2 and a3 is retained.

(3) analyzing a cause of the sub-region, and conducting a plurality of additional repetitive experiments after solving the cause. For example, if there is a large difference in measured soil humidity during two repetitive experiments, it may be that when a rice field is irrigated before, a uniformity of irrigation in different regions is not guaranteed, which leads to a difference in a subsequent experimental process. So, after solving the uniformity of irrigation, the repetitive experiments may be conducted again.

The monitoring device collects the physicochemical feature and uploads the physicochemical feature to the processor at a first collection frequency, the first collection frequency is issued by the processor to the monitoring device within a first predetermined period, and the first collection frequency is determined based on a free resource bandwidth of the processor in a future time period, and the first predetermined period is determined based on a change rate of a free resource bandwidth of the processor in a historical time period.

In some embodiments, the first collection frequency is positively correlated with the free resource bandwidth of the processor in a future time period, e.g., the greater the free resource bandwidth in the future time period, the greater the first collection frequency may be.

In some embodiments, the first predetermined period is negatively correlated with a change rate of a free resource bandwidth of the processor in a historical time period, the greater the change rate of the free resource bandwidth of the processor in the historical time period, the shorter the first predetermined period may be.

In some embodiments, the processor may periodically calculate the change rate of the free resource bandwidth in the historical time period and store the change rate in the storage unit. The greater the change rate, the shorter the period may be set, and the processor can adapt to a high-frequency change situation and adjust the first predetermined period accordingly more quickly by calculating and storing the change rate.

Step 160, obtaining experimental parameters and experimental yield data of each of the one or more experimental processings, and optimized yield data of the optimized fertilization processing, and storing the experimental parameters, the experimental yield data, and the optimized yield data in the storage unit.

The one or more experimental processings refer to experimental processings that may be used for subsequent regression analysis after the predetermined processing is performed on the abnormal sub-region. For example, if the processor processes the abnormal sub-region based on the predetermined processing according to (1), then the one or more experimental processings may include experimental processing of other sub-regions except the abnormal sub-region. As another example, if the processor processes the abnormal sub-region based on the predetermined processing according to (2), the one or more experimental processings may further include: an experimental processing obtained after removing repetitive experiments containing abnormal data in the abnormal sub-region.

The experimental yield data is crop yield data corresponding to the experimental processing at the end of the intelligent planting experiment. The optimized yield data is crop yield data corresponding to the optimized fertilization processing at the end of the intelligent planting experiment. In some embodiments, the processor may obtain, via the monitoring device (e.g., a weight sensor), the experimental yield data and the optimized yield data of the intelligent planting experiment at the time of harvesting.

Step 170, determining the model for reduced fertilization of nitrogen, phosphorus, and potassium nutrients and generating a fertilizer formula based on the experimental parameters, the experimental yield data, and the optimized yield data through a regression model, and storing the model for reduced fertilization the nitrogen, phosphorus, and potassium nutrients in the storage unit.

The regression model is obtained by the processor from the storage unit, and the model for reduced fertilization of nitrogen, phosphorus, and potassium nutrients includes a model for reduced fertilization of phosphorus and potassium nutrients and a model for reduced fertilization of nitrogen nutrient.

In some embodiments, the processor may determine the model for reduced fertilization of phosphorus and potassium nutrients based on a dosage of a conditioner, a reduced fertilization ratio of a phosphorus nutrient, and a reduced fertilization ratio of a potassium nutrient of each experimental processing in the first experiment scheme, and experimental yield data of each experimental processing and optimized yield data of the optimized fertilization processing.

In some embodiments, the processor may determine the model for reduced fertilization of nitrogen nutrient based on a dosage of a conditioner, a fertilization ratio of a controlled-release nitrogen fertilizer, and a reduced fertilization ratio of a nitrogen nutrient of each experimental processing in the second experimental scheme, and experimental yield data of each experimental processing and the optimized yield data of the optimized fertilization processing.

In some embodiments, different types of rice correspond to different models for reduced fertilization of phosphorus and potassium nutrients, and in the model for reduced fertilization of phosphorus and potassium nutrients, the dosage of the conditioner is positively correlated with the reduced fertilization ratio of the phosphorus nutrient and the reduced fertilization ratio of the potassium nutrient; and different types of rice correspond to different models for reduced fertilization of nitrogen nutrient, and in the model for reduced fertilization of nitrogen nutrient, the reduced fertilization ratio of the nitrogen nutrient is correlated with the dosage of the conditioner, the fertilization ratio of the controlled-release nitrogen fertilizer, and the reduced fertilization ratio of the nitrogen nutrient.

For example, the processor may conduct the intelligent planting experiment based on the experimental scheme and the fertilization dosage, statistically count a rice yield of each experimental processing and optimized fertilization processing, and then fit each experimental processing using the regression model to obtain a mathematical equation, substituting rice yield data of the optimized fertilization processing into the equation to obtain the model for reduced fertilization ratio of the nitrogen, phosphorus, and potassium nutrients;

Only by way of example, the model for reduced fertilization of nitrogen, phosphorus, and potassium nutrients may include:

(1) a Model for Reduced Fertilization of Phosphorus and Potassium Nutrients:

in some embodiments, using the conditioner, the phosphorus nutrient, and the potassium nutrient as three experimental factors, and eight dosage levels and eight reduced fertilization ratio levels in step 140 as experimental levels, and using a U8(8) uniform experimental design to obtain 8 experimental processings, thereby obtaining the first experimental scheme, and setting the optimized fertilization processing (CK) and a non-fertilization processing, so there are a total of 10 experimental processings, in each experimental processing, a nitrogen fertilizer was used in three times before transplanting, during tillering, and during spike differentiation period, respectively, a phosphorus fertilizer and a potassium fertilizer were used all at once as basic formula, and then conducting an intelligent planting experiment on the 10 experimental processings, controlling an area of a predetermined sub-region of each intelligent planting unit at 20-30 $m^2$ and adopting a randomized block design, and repeating each processing three times, and counting a yield when the rice was ripe, and results were shown in Table 1:

TABLE 1

Results of field planting experiments using the conditioner, the phosphorus nutrient, and the potassium nutrient as three experimental factors

| Processing No. | A dosage of a conditioner (kg/mu) | A reduced fertilization ratio of a phosphorus nutrient (%) | A reduced fertilization ratio of a potassium nutrient (%) | A yield of early rice (kg/mu) | A yield of late rice (kg/mu) |
|---|---|---|---|---|---|
| Non-fertilization | 0 | 0 | 0 | 304 | 347 |
| Optimized fertilization (CK) | 0 | 0 | 0 | 460 | 551 |
| T1 | 0 | 27 | 42 | 486 | 580 |
| T2 | 30 | 63 | 28 | 462 | 553 |
| T3 | 60 | 18 | 14 | 467 | 560 |
| T4 | 90 | 54 | 0 | 431 | 516 |
| T5 | 120 | 9 | 49 | 494 | 592 |
| T6 | 150 | 45 | 35 | 471 | 564 |
| T7 | 180 | 0 | 21 | 467 | 559 |
| T8 | 210 | 36 | 7 | 437 | 523 |

By fitting experimental yield data obtained of each experimental processing with a dosage of the conditioner and a reduced fertilization ratio of nutrients of each experimental processing using a ternary primary regression model, a mathematical equation between the dosage of the conditioner, the reduced fertilization ratio of the phosphorus nutrient, the reduced fertilization ratio of the potassium nutrient, and the yield is obtained, for example, a mathematical equation of early rice: $Y=-0.207\ P-0.456K+0.227\ T+458.25$ (wherein Y is a yield of rice, P is the reduced fertilization ratio of the phosphorus nutrient, K is the reduced fertilization ratio of the potassium nutrient, and T is the dosage of the conditioner); and a mathematical equation of late rice: $Y=-0.238\ P-0.552K+0.269\ T+548.58$, finally substituting yield data of early rice of 460 kg/mu and yield data of late rice of 550 kg/mu of the optimized fertilization processing into the above mathematical equations to obtain a mathematical model of the dosage of the conditioner, the reduced fertilization ratio of the phosphorus nutrient, and the reduced fertilization ratio of the potassium nutrient, and specific results were shown as follows:

a model for reduced fertilization of the phosphorus and potassium nutrients for early rice: $T=0.91\ P+2.01K+7.71$ ($R^2=0.98$, $P=0.00084$); a model for reduced fertilization of the phosphorus and potassium nutrients for middle rice or late rice: $T=0.88\ P+2.05K+9$ ($R^2=0.90$, $P=0.019$), wherein T is the dosage of the conditioner, P is the reduced fertilization of the phosphorus nutrient, K is the reduced fertilization of the potassium nutrient, $P\le65\%$, $K\le50\%$;

(2) A Model for Reduced Fertilization of the Nitrogen Nutrient:

in some embodiments, using the conditioner, the controlled-release nitrogen fertilizer, and the nitrogen nutrient as three experimental factors, and adopting a "3414" experimental design, and using four dosage levels of the conditioner, four fertilization ratio levels of the controlled-release urea, and four reduced fertilization ratio levels of the nitrogen nutrient in step 140 as the experimental level, adopting the "3414" experimental design to obtain 14 experimental processings and setting the optimized fertilization processing as a control, so there are a total of 15 experimental processings. In the optimized fertilization processing, the nitrogen fertilizer was used in three times before transplanting, during tillering, and during spike differentiation period respectively, while the phosphate fertilizer and the potassium fertilizer were used all at once, and other experimental processings were all one-time fertilization. Then conducting the intelligent field planting experiment on the 15 experimental processings, controlling an area of a predetermined sub-region of each target planting unit to be 20-30 $m^2$, adopting a randomized block design, each processing was repeated three times. Counting a yield when the rice was ripe, and specific yield data are shown in Table 2:

TABLE 2

Results of field planting experiments using the conditioner, the controlled-release nitrogen fertilizer, and the nitrogen nutrients as experimental factors

| Processing No. | A dosage of a conditioner (kg/mu) | A fertilization ratio of a controlled-release urea (%) | A reduced fertilization ratio of a nitrogen nutrient (%) | A yield of early rice (kg/mu) | A yield of late rice (kg/mu) |
|---|---|---|---|---|---|
| Optimized fertilization | 0 | 0 | 0 | 460 | 551 |
| T1 | 0 | 0 | 0 | 392 | 468 |
| T2 | 0 | 50 | 30 | 420 | 503 |
| T3 | 50 | 50 | 30 | 455 | 544 |
| T4 | 100 | 0 | 30 | 428 | 512 |
| T5 | 100 | 25 | 30 | 442 | 529 |
| T6 | 100 | 50 | 30 | 465 | 556 |
| T7 | 100 | 75 | 30 | 480 | 576 |
| T8 | 100 | 50 | 0 | 490 | 586 |
| T9 | 100 | 50 | 15 | 473 | 567 |
| T10 | 100 | 50 | 45 | 446 | 533 |
| T11 | 150 | 50 | 30 | 477 | 571 |
| T12 | 50 | 25 | 30 | 432 | 517 |
| T13 | 50 | 50 | 15 | 463 | 562 |
| T14 | 100 | 25 | 15 | 470 | 560 |

By fitting experimental yield data obtained of each experimental processing and a dosage of the conditioner, a fertilization ratio of controlled-release urea, and a reduced fertilization ratio of the nitrogen nutrient of each experimental processing using a ternary quadratic regression model, a mathematical equation between the dosage of the conditioner, the fertilization ratio of the controlled-release urea, and the reduced fertilization ratio of the nitrogen nutrient and yield is obtained, specifically, a mathematic equation of early rice: $Y=-0.002\ T^2-0.0033C^2-0.013N^2+0.92\ T+0.88C-0.35N-0.0025TC-0.0053TN+0.011CN+393.33$, wherein Y is a yield of rice, N is the reduced fertilization ratio of the nitrogen nutrient, T is the dosage of the conditioner, and C is the fertilization ratio of the controlled-release nitrogen fertilizer; and a mathematical equation of late rice: $Y=-0.0026\ T^2-0.0039C^2-0.019N^2+0.95\ T+1.53C-0.47N-0.0042TC+0.0012TN+0.0015CN+469.16$;

finally, substituting yield data of early rice of 460 kg/mu and late rice of 550 kg/mu obtained from the optimized fertilization processing into the above equations to calculate a mathematical model of the reduced fertilization ratio of the nitrogen nutrient, the dosage of the conditioner, and the fertilization ratio of the controlled-release urea including: a model for reduced fertilization of nitrogen nutrient for early rice: $N=(-0.11\ T2-0.08C2+74.75\ T+55.85C-0.35\ T\ C-4847.55)\frac{1}{2}-(0.2\ T-0.41C+13.21)$ $(R2=0.98, P=0.0046)$; a model for reduced fertilization of nitrogen nutrient for late rice or middle rice: $N=(-0.13\ T2-0.2C2+47.9\ T+77.28C-0.21\ TC-4035)\frac{1}{2}+(0.032\ T+0.038C-11.94)$ $(R2=0.98, P=0.0051)$; where N is the reduced fertilization ratio of the nitrogen nutrient, T is the dosage of the conditioner, C is the fertilization ratio of the controlled-release nitrogen, with $40\leq T\leq 250$ kg/mu and $20\% \leq C\leq 85\%$.

The fertilizer formula is a fertilizer application formula that is better suited to the target planting unit.

In some embodiments, the processor may determine the fertilizer formula based on the basic formula for fertilization, the reduced fertilization ratio of the phosphorus nutrient, the reduced fertilization ratio of the potassium nutrient, the fertilization ratio of the controlled-release nitrogen fertilizer, and the dosage of the conditioner and the reduced fertilization ratio of the nitrogen nutrient determined by the model for reduced fertilization of nitrogen, phosphorus, and potassium nutrients, more description of which can be found in FIG. 3 and its related description.

In some embodiments of the present disclosure, the model for reduced fertilization of the phosphorus and potassium nutrients is obtained by the uniform experimental design, which drastically reduces a count of experiments while fully considering a reduced fertilization gradient of the phosphorus and potassium nutrients, and the model for reduced fertilization of the nitrogen nutrients obtained by adopting the "3414", $L16(4^3)$, or $L25(5^3)$ orthogonal experimental design, not only quantifies the interaction effects between the conditioner and the controlled-release nitrogen fertilizers, but also effectively reduces a number of experiments. Without reducing the yield of rice, by substituting the yield of the optimized fertilization processing to the regression model, an equilibrium point between the fertilization ratio of the controlled-release fertilizer, the dosage of the conditioner, and the reduced fertilization of the nitrogen, phosphorus, and potassium nutrients was found, and the mathematical relationship model between the fertilization ratio of the controlled-release fertilizer, the dosage of the conditioner, and the reduced fertilization of the nitrogen, phosphorus, and potassium nutrient was clearly proposed, which has important reference significance and value for applying the controlled-release fertilizer and conditioner to large-scale farming and even the development of the whole industry of the controlled-release fertilizer and conditioner.

Also, in some embodiments of the present disclosure, a dosage range of the conditioner ranges from 0–250 kg/mu, a fertilization ratio range of the controlled-release nitrogen fertilizer ranges from 20%-85%, and a reduced fertilization ratio range of the nitrogen, phosphorus, and potassium nutrients ranges from 0%-50%, 0%-65%, and 0%-50%, respectively. This is because, if the fertilization ratio of the controlled-release fertilizer is too low, then the controlled-release fertilizer may not be reduced further, and if the reduced fertilization ratio of the nitrogen, phosphorus, and potassium nutrients is too high, a nutrient requirement of rice can not be satisfied, so the ranges try to balance the fertilization ratio of the controlled-release fertilizer between the nutrient requirement of rice, so as to ensure the accuracy of the model, and truly reduce fertilizers without reducing yields.

FIG. 2 is a schematic diagram illustrating an exemplary difference prediction model according to some embodiments of the present disclosure.

In some embodiments, a processor may determine a fertility difference distribution 230 based on soil features 211 of a predetermined point at one or more time points through a difference prediction model 220, and the difference prediction model 220 is a machine learning model.

For a more detailed description of the one or more time points, predetermined point, soil feature, and fertility difference distribution, please see the description associated with FIG. 1.

The difference prediction model refers to a machine learning model for the fertility difference distribution. In some embodiments, the difference prediction model may be a machine learning model with a customized structure as described below, or it may be a machine learning model with another structure. For example, the machine learning model may be a Neural Network (NN), Deep Neural Networks model (DNN), Convolutional Neural Networks (Convolutional Neural Networks, CNN), etc., or any combination thereof.

As shown in FIG. 2, in some embodiments, an input to the difference prediction model 220 may include the soil features 211 of the predetermined point at the one or more time points, and an output may include the fertility difference distribution 230 of a target planting unit.

In some embodiments, the input to the difference prediction model 220 may also include historical experimental data 212 of the target planting unit.

The historical experimental data refers to data related to historical intelligent planting experiments. In some embodiments, the historical experimental data includes a historical fertilization frequency and historical fertilization dosage of different types of fertilizers at different predetermined points of the target planting unit.

In some embodiments, the processor may obtain the historical experimental data from a storage unit.

In some embodiments, the input to the difference prediction model 220 may also include light features 213 at the one or more time points.

The light features are light-related data that may affect plant growth. For example, the light features may include a light intensity, light duration, light direction, and light quality (e.g., different wavelengths of light), etc.

In some embodiments, the processor may determine the light features 213 based on light sensing data captured by a light sensor deployed on a surface of the target planting unit.

As shown in FIG. 2, in some embodiments, the difference prediction model 220 may include a soil feature embedding layer 221, a light feature embedding layer 222, and a difference predicting layer 225.

In some embodiments, the soil feature embedding layer may be used to determine a soil feature embedding vector 223 based on the historical experimental data 212 and the soil features 211 of the predetermined point at the one or more time points. In some embodiments, the soil feature embedding layer 223 may be Convolutional Neural Networks (CNN).

The soil feature embedding vector is data that reflects a feature and attributes of the soil features and historical experimental data in different data dimensions.

In some embodiments, the light feature embedding layer may be used to determine a light feature embedding vector 224 based on the light features 213 at the one or more time points. In some embodiments, the light feature embedding layer 222 may be Convolutional Neural Networks (CNN).

The light feature embedding vector is data that reflects a feature and attributes of the light features in different data dimensions.

In some embodiments, the difference predicting layer may be used to determine the fertility difference distribution 230 based on the soil feature embedding vector 223, or the soil feature embedding vector 223 and the light feature embedding vector 224. In some embodiments, the difference predicting layer 225 may be a neural network (NN).

In some embodiments, the soil feature embedding layer, the light feature embedding layer, and the difference predicting layer may be obtained by a joint training.

A training sample for training the difference prediction model may include sample historical experimental data, sample soil features of a predetermined point at one or more time points within a first historical time period, and sample light features at the one or more time points within the first historical time period, and a label may include an actual fertility difference distribution at a first historical time point corresponding to the training sample.

In some embodiments, the training sample and label may be obtained based on historical data. The first historical time point is after the first historical time period.

A training process may include: inputting the sample historical experimental data, the sample soil features of the predetermined point at the one or more time points within the first historical time period into the soil feature embedding layer to obtain a sample soil feature embedding vector; inputting the sample light features at the one or more time points within the first historical time period to the light feature embedding layer to obtain a sample light feature embedding vector; inputting the sample soil feature embedding vector and the sample light feature embedding vector into the difference predicting layer to obtain an initial fertility difference distribution; constructing a loss function based on the initial fertility difference distribution and label, and using the loss function to synchronously update parameters of the soil feature embedding layer, the light feature embedding layer, and the difference predicting layer; then obtaining a trained difference prediction model by parameter update.

In some embodiments of the present disclosure, predicting the fertility difference distribution of the target planting unit by the difference prediction model can utilize the self-learning ability of a machine learning model to improve the efficiency and accuracy of predicting the fertility difference distribution; by setting the model to different layers to separately process different data, the data processing efficiency can be improved; in addition, since the historical intelligent planting experiments may have an effect on the target planting unit, and light has an effect on the change of soil fertility, using the historical experimental data and light feature as input to the difference prediction model can improve the accuracy of the difference prediction model.

One or more embodiments of the present disclosure provide a system for generating a fertilizer formula, including a processor, a storage unit, and a monitoring device communicatively connected to the processor.

The processor may be used to process information and/or data related to application scenarios of the system for generating fertilizer formula, for example, monitoring data, experimental yield data, etc. In some embodiments, the processor may process data, information, and/or a processing result obtained from other devices or components of a system, and execute program instructions based on such data, information, and/or processing result to perform one or more functions described in the present disclosure.

In some embodiments, the processor may obtain a basic formula for fertilization.

In some embodiments, the processor may obtain the monitoring data based on a monitoring device and determine a soil feature of a predetermined point based on the monitoring device.

In some embodiments, the processor may determine an experimental scheme and experimental parameters based on the soil feature and an experimental design, determine a fertilization dosage based on the experimental parameters and the basic formula for fertilization, and conduct an intelligent planting experiment based on the fertilization dosage and the experimental scheme.

In some embodiments, the processor may obtain experimental parameters and experimental yield data of each of the one or more experimental processings, and optimized yield data of the optimized fertilization processing, and store the experimental parameters, the experimental yield data and the optimized yield data in the storage unit; and determine a model for reduced fertilization of nitrogen, phosphorus, and potassium nutrients and generate the fertilizer formula based on the experimental parameters, the experimental yield data, and the optimized yield through a regression model, and store the model for reduced fertilization of nitrogen, phosphorus, and potassium nutrients in the storage unit.

The monitoring device may be a device for obtaining the monitoring data. In some embodiments, the monitoring device may include a sensor, such as a temperature sensor, a humidity sensor, a pH sensor, or the like. In some embodiments, the monitoring device may be deployed at one or more predetermined points of a target planting unit.

The storage unit may store data, instructions, and/or any other information. In some embodiments, the storage unit may store the regression model, the experimental yield data, the optimized yield data, and the model for reduced fertilization of nitrogen, phosphorus, and potassium nutrients, etc. The storage unit may include one or more storage components, each storage component may be a separate device or part of another device. In some embodiments, the storage unit may include random access memory (RAM), read-only memory (ROM), removable memory, etc., or any combination thereof. In some embodiments, the storage unit may be communicatively connected to the processor.

One or more embodiments of the present disclosure provide a device for generating a fertilizer formula, including at least one processor and at least one memory; wherein the at least one memory is configured to store computer instructions; and the at least one processor is configured to execute at least some of the computer instructions in the computer instructions to implement the method for generating a fertilizer formula described above.

One or more embodiments of the present disclosure provide a computer-readable storage medium storing computer instructions, and when the computer reads the computer instructions in the storage medium, the computer executes the method for generating a fertilizer formula as described above.

FIG. 3 is a flowchart illustrating an exemplary method for generating a fertilizer formula according to some embodiments of the present disclosure. In some embodiments, a process 300 may be executed by a processor. As shown in FIG. 3, the process 300 includes following steps.

Step 310, obtaining a basic formula for fertilization.

In some embodiments, the processor may access relevant information pre-stored in a storage unit to determine the basic formula for fertilization. Exemplary relevant information may include the Technical Specification for Soil Formula Fertilizer Measurement (Revised 2011)

In some embodiments, the basic formula for fertilization is the same as a basic formula for fertilization in step 110. For example, a basic formula of early rice is N: 12 kg/mu; $P_2O_5$: 6 kg/mu; $K_2O$: 10 kg/mu, and a basic formula for late rice base formulation is N: 14 kg/mu; $P_2O_5$:6 kg/mu; $K_2O$: 10 kg/mu.

In some embodiments, a controlled-release nitrogen fertilizer used by the processor is a resin-coated urea; and the basic formula for fertilization includes a basic formula for early rice, and late rice or middle rice.

The basic formula for fertilization for early rice is a fertilization dosage of pure nitrogen (N) is 10–15 kg/mu, a fertilization dosage of pure phosphorus ($P_2O_5$) is 5–8 kg/mu, and a fertilization dosage of pure potassium ($K_2O$) is 8–12 kg/mu; and the basic formula for fertilization for late or middle rice is a fertilization dosage of pure nitrogen (N) is 12–18 kg/mu, a fertilization dosage of pure phosphorus ($P_2O_5$) is 5–8 kg/mu, and a fertilization dosage of pure potassium ($K_2O$) is 8–12 kg/mu. A controlled-release period of a controlled-release nitrogen fertilizer selected for the early rice is 50–75 days, and a controlled-release period of a controlled-release nitrogen fertilizer selected for the late rice or middle rice is 70–105 days.

Step 320, obtaining monitoring data based on a monitoring device.

Step 330, determining a soil feature of a predetermined point based on the monitoring data.

For a more detailed description of the monitoring device, the monitoring data, the predetermined point, and the soil feature, please see FIG. 1 and its related description.

Step 340, determining a reduced fertilization ratio of a phosphorus nutrient and a reduced fertilization ratio of a potassium nutrient based on a phosphorus fertilizer price feature, a potassium fertilizer price feature, the soil feature, and a climatic feature, and determining a dosage of a conditioner through a model for reduced fertilization of phosphorus and potassium nutrients.

The phosphorus and potassium fertilizer price features may include the cost-effectiveness of a phosphorus fertilizer and a potassium fertilizer.

The climatic feature is a climatic or environmental factor that may affect the growth and development of crops. For example, the climatic feature may include a temperature, a light, a humidity, a precipitation, etc.

In some embodiments, the processor may obtain the phosphorus fertilizer price feature, the potassium fertilizer price feature, the soil feature, and the climate feature from one or more Internet of Things units, the processor being communicatively connected to the Internet of Things units. The Internet of Things unit is a basic constituent unit of the Internet of Things system, including a sensor and an actuator, and is capable of accomplishing data acquisition, processing, and transmission of the Internet of Things system.

In some embodiments, the processor determines the reduced fertilization ratio of the phosphorus nutrient and the reduced fertilization ratio of the potassium nutrient based on the phosphorus fertilizer price feature, the potassium fertilizer price feature, the soil feature, and the climatic feature by querying a preset table of reduced fertilization of phosphorus and potassium. A plurality of different sets of phosphorus fertilizer price features, potassium fertilizer price features, soil features, and climatic features are stored in the preset table of reduced fertilization of phosphorus and potassium, and a reduced fertilization ratio of the phosphorus nutrient and a reduced fertilization ratio of the potassium nutrient corresponding to the above four features. The preset table of reduced fertilization of phosphorus and potassium may be pre-set based on prior knowledge or historical data.

In some embodiments, the processor may determine the dosage of the conditioner based on the model for reduced fertilization of the phosphorus and potassium nutrients, the reduced fertilization ratio of the phosphorus nutrient, and the reduced fertilization ratio of the potassium nutrient. In some embodiments, when the reduced fertilization ratio of the phosphorus nutrient and the reduced fertilization ratio of the potassium nutrient are 0, for example, a reduced fertilization ratio of the phosphorus nutrient for the early rice and late rice is set to 50% and a reduced fertilization ratio of the potassium nutrient is set to 35%, and if a model for reduced fertilization of the phosphorus and potassium nutrients for the early rice is T=0.91 P+2.01K+7.71, based on a calculation result, it may be known that the dosage of conditioner for the early rice is 123 kg/mu; if a model for reduced fertilization of the phosphorus and potassium nutrients for the late rice is T=0.88 P+2.05K+9, based on a calculation result, it may be known that the dosage of conditioner for the late rice is 125 kg/mu.

Step 350, determining a fertilization ratio of a controlled-release fertilizer based on a controlled-release fertilizer price feature, the soil feature, and the climatic feature, and determining a reduced fertilization ratio of a nitrogen nutrient based on a model for reduced fertilization of nitrogen nutrient and the dosage of the conditioner.

The controlled-release fertilizer price feature may include the cost-effectiveness of the controlled-release fertilizer.

In some embodiments, the processor determines the fertilization ratio of the controlled-release fertilizer by querying a preset table of controlled-release fertilizer based on the controlled-release fertilizer price feature, the soil feature, and the climate feature. A plurality of different sets of controlled-release fertilizer price features, soil features, and climatic features are stored in the preset table of controlled-release fertilizer, and fertilization ratios of the controlled-release fertilizer corresponding to the above three features. The preset table of controlled-release fertilizer may be pre-set based on a priori knowledge or historical data.

In some embodiments, the processor may determine the reduced fertilization ratio of the nitrogen nutrient based on the fertilization ratio of the controlled-release fertilizer, the model for reduced fertilization of nitrogen nutrient, and the dosage of the conditioner.

In some embodiments, if a fertilization ratio of the controlled-release fertilizer for the early rice and later rice (e.g., a fertilization ratio of controlled-release urea) is set to be 50%, and a dosage of the conditioner is 123 kg/mu and 125 kg/mu, respectively, and if a model for reduced fertilization of nitrogen nutrient for the early rice is N=(−0.11 $T^2$−0.08$C^2$+74.75 T+55.85C−0.35TC−4847.55)$^{1/2}$−(0.2 T−0.41C+13.21), based on a calculation result, it may be seen that a fertilization ratio of the nitrogen nutrient for the early rice is 39%; if a model for reduced fertilization of nitrogen nutrient for the late rice is N=(−0.13 $T^2$−0.2$C^2$+ 47.9 T+77.28C−0.21TC−4035)$^{1/2}$+(0.032 T+0.038C− 11.94), it may be seen that a reduced fertilization ratio of the nitrogen nutrient for the late rice is 38%.

Step 360, generating the fertilizer formula based on the basic formula for fertilization, the reduced fertilization ratio of the phosphorus nutrient, the reduced fertilization ratio of the potassium nutrient, the dosage of the conditioner, the fertilization ratio of the controlled-release nitrogen fertilizer, and the reduced fertilization ratio of the nitrogen nutrient, and storing the fertilizer formula in a storage unit.

In some embodiments, based on the model for reduced fertilization of phosphorus and potassium nutrients and the model for reduced fertilization of nitrogen nutrient, for the early rice, a fertilization ratio of the controlled-release urea is calculated to be 30%-70%, and a reduced fertilization ratio of the nitrogen nutrient is calculated to be 3%-47%, a reduced fertilization ratio of the phosphorus nutrient is 20%-50%, and a reduced fertilization ratio of the potassium nutrient is 10%-40% if a dosage of the conditioner is 46–134 kg/mu; for the late rice, a fertilization ratio of the controlled-release urea is 30%-70%, a reduced fertilization ratio of the nitrogen nutrient is 4%-45%, a reduced fertilization ratio of the phosphorus nutrient is 20%-50%, and a reduced fertilization ratio of the potassium nutrient is 10%-40% if a dosage of the conditioner is 47–135 kg/mu, then a calculation result shows that for the early rice, a reduced fertilization dosage of the nitrogen nutrient is 0.36–5.67%, a reduced fertilization dosage of the phosphorus nutrient is 1.2–3 kg/mu, a reduced fertilization dosage of the potassium nutrient is 1~4 kg/mu; and for the late rice, a reduced fertilization dosage of the nitrogen nutrient is 0.56–6.32 kg/mu, a reduced fertilization dosage of the phosphorus nutrient is 1.2–3 kg/mu, a reduced fertilization dosage of the potassium nutrient is 1~4 kg/mu, so for the early rice, a fertilization dosage of pure nitrogen (N) is 6.33–11.64 kg/mu, a fertilization dosage of pure phosphorus ($P_2O_5$) is 3–4.8 kg/mu, and a fertilization dosage of pure potassium ($K_2O$) is 6−9 kg/mu; and for the later rice, a fertilization dosage of pure nitrogen (N) is 7.68–13.44 kg/mu, a fertilization dosage of pure phosphorus ($P_2O_5$) is 3–4.8 kg/mu, and a fertilization dosage of pure potassium ($K_2O$) is 6−9 kg/mu. Conducting an intelligent planting experiment with each experimental field controlled at 20–30 $m^2$ and using a randomized block design, each experimental example was repeated 3 times, and specific fertilizer formulas are shown in Tables 3 and 4 below.

CK is an optimized fertilization processing, for the early rice, a fertilization dosage of pure nitrogen (N) is 12 kg/mu, a fertilization dosage of pure phosphorus ($P_2O_5$) is 6 kg/mu, and a fertilization dosage of pure potassium ($K_2O$) is 10 kg/mu; for the late rice, a fertilization dosage of pure nitrogen (N) is 14 kg/mu, a fertilization dosage of pure phosphorus ($P_2O_5$) is 6 kg/mu, and a fertilization dosage of pure potassium ($K_2O$) is 10 kg/mu. In the optimized fertilization processing, the nitrogen fertilizer was used three times before transplanting, during tillering, and during spike differentiation period respectively, and the phosphorus fertilizer and potassium fertilizer were used all once as a basic fertilizer, and the rest of the fertilizers were used all at once:

TABLE 3

| Fertilizer formula for early rice | | | | | | | | | | | |
|---|---|---|---|---|---|---|---|---|---|---|---|
| Experiment No. | Dosage of a conditioner (kg/mu) | Fertilization ratio of a controlled-release urea (%) | Reduced fertilization ratio of nutrients (%) | | | Reduced fertilization dosage of nutrients (kg/mu) | | | An actual dosage of nutrients used (kg/mu) | | |
| | | | N | $P_2O_5$ | $K_2O$ | N | $P_2O_5$ | $K_2O$ | N | $P_2O_5$ | $K_2O$ |
| CK | 0 | 0 | 0 | 0 | 0 | 0 | 0 | 0 | 12 | 6 | 10 |
| No. 1 | 46 | 30 | 3 | 20 | 10 | 0.36 | 1.20 | 1.00 | 11.64 | 4.80 | 9.00 |
| No. 2 | 46 | 40 | 6 | 20 | 10 | 0.72 | 1.20 | 1.00 | 11.28 | 4.80 | 9.00 |
| No. 3 | 46 | 50 | 10 | 20 | 10 | 1.22 | 1.20 | 1.00 | 10.78 | 4.80 | 9.00 |
| No. 4 | 46 | 60 | 24 | 20 | 10 | 2.82 | 1.20 | 1.00 | 9.18 | 4.80 | 9.00 |
| No. 5 | 46 | 70 | 34 | 20 | 10 | 4.04 | 1.20 | 1.00 | 7.96 | 4.80 | 9.00 |
| No. 6 | 75 | 30 | 15 | 30 | 20 | 1.82 | 1.80 | 2.00 | 10.18 | 4.20 | 8.00 |
| No. 7 | 75 | 40 | 23 | 30 | 20 | 2.74 | 1.80 | 2.00 | 9.26 | 4.20 | 8.00 |
| No. 8 | 75 | 50 | 30 | 30 | 20 | 3.61 | 1.80 | 2.00 | 8.39 | 4.20 | 8.00 |
| No. 9 | 75 | 60 | 37 | 30 | 20 | 4.42 | 1.80 | 2.00 | 7.58 | 4.20 | 8.00 |
| No. 10 | 75 | 70 | 43 | 30 | 20 | 5.18 | 1.80 | 2.00 | 6.82 | 4.20 | 8.00 |
| No. 11 | 104 | 30 | 26 | 40 | 30 | 3.10 | 2.40 | 3.00 | 8.90 | 3.60 | 7.00 |
| No. 12 | 104 | 40 | 31 | 40 | 30 | 3.76 | 2.40 | 3.00 | 8.24 | 3.60 | 7.00 |
| No. 13 | 104 | 50 | 37 | 40 | 30 | 4.40 | 2.40 | 3.00 | 7.60 | 3.60 | 7.00 |
| No. 14 | 104 | 60 | 42 | 40 | 30 | 5.01 | 2.40 | 3.00 | 6.99 | 3.60 | 7.00 |
| No. 15 | 104 | 70 | 47 | 40 | 30 | 5.61 | 2.40 | 3.00 | 6.39 | 3.60 | 7.00 |
| No. 16 | 134 | 30 | 30 | 50 | 40 | 3.66 | 3.00 | 4.00 | 8.34 | 3.00 | 6.00 |
| No. 17 | 134 | 40 | 35 | 50 | 40 | 4.19 | 3.00 | 4.00 | 7.81 | 3.00 | 6.00 |
| No. 18 | 134 | 50 | 39 | 50 | 40 | 4.70 | 3.00 | 4.00 | 7.30 | 3.00 | 6.00 |
| No. 19 | 134 | 60 | 43 | 50 | 40 | 5.19 | 3.00 | 4.00 | 6.81 | 3.00 | 6.00 |
| No. 20 | 134 | 70 | 47 | 50 | 40 | 5.67 | 3.00 | 4.00 | 6.33 | 3.00 | 6.00 |

TABLE 4

Fertilizer formula for late rice

| Experiment No. | Dosage of a conditioner (kg/mu) | Fertilization ratio of controlled-release fertilizer (%) | Reduced fertilization ratio of nutrients (%) | | | Reduced fertilization dosage of nutrients (kg/mu) | | | Actual dosage of nutrients used (kg/mu) | | |
|---|---|---|---|---|---|---|---|---|---|---|---|
| | | | N | $P_2O_5$ | $K_2O$ | N | $P_2O_5$ | $K_2O$ | N | $P_2O_5$ | $K_2O$ |
| CK | 0 | 0 | 0 | 0 | 0 | 0 | 0 | 0 | 14 | 6 | 10 |
| No. 21 | 47 | 30 | 4 | 20 | 10 | 0.56 | 1.20 | 1.00 | 13.44 | 4.80 | 9.00 |
| No. 22 | 47 | 40 | 9 | 20 | 10 | 1.21 | 1.20 | 1.00 | 12.79 | 4.80 | 9.00 |
| No. 23 | 47 | 50 | 20 | 20 | 10 | 2.77 | 1.20 | 1.00 | 11.23 | 4.80 | 9.00 |
| No. 24 | 47 | 60 | 27 | 20 | 10 | 3.82 | 1.20 | 1.00 | 10.18 | 4.80 | 9.00 |
| No. 25 | 47 | 70 | 33 | 20 | 10 | 4.63 | 1.20 | 1.00 | 9.37 | 4.80 | 9.00 |
| No. 26 | 76 | 30 | 15 | 30 | 20 | 2.03 | 1.80 | 2.00 | 11.97 | 4.20 | 8.00 |
| No. 27 | 76 | 40 | 24 | 30 | 20 | 3.30 | 1.80 | 2.00 | 10.70 | 4.20 | 8.00 |
| No. 28 | 76 | 50 | 30 | 30 | 20 | 4.23 | 1.80 | 2.00 | 9.77 | 4.20 | 8.00 |
| No. 29 | 76 | 60 | 35 | 30 | 20 | 4.96 | 1.80 | 2.00 | 9.04 | 4.20 | 8.00 |
| No. 30 | 76 | 70 | 40 | 30 | 20 | 5.57 | 1.80 | 2.00 | 8.43 | 4.20 | 8.00 |
| No. 31 | 106 | 30 | 25 | 40 | 30 | 3.49 | 2.40 | 3.00 | 10.51 | 3.60 | 7.00 |
| No. 32 | 106 | 40 | 31 | 40 | 30 | 4.36 | 2.40 | 3.00 | 9.64 | 3.60 | 7.00 |
| No. 33 | 106 | 50 | 36 | 40 | 30 | 5.06 | 2.40 | 3.00 | 8.94 | 3.60 | 7.00 |
| No. 34 | 106 | 60 | 40 | 40 | 30 | 5.63 | 2.40 | 3.00 | 8.37 | 3.60 | 7.00 |
| No. 35 | 106 | 70 | 44 | 40 | 30 | 6.11 | 2.40 | 3.00 | 7.89 | 3.60 | 7.00 |
| No. 36 | 135 | 30 | 30 | 50 | 40 | 4.24 | 3.00 | 4.00 | 9.76 | 3.00 | 6.00 |
| No. 37 | 135 | 40 | 35 | 50 | 40 | 4.92 | 3.00 | 4.00 | 9.08 | 3.00 | 6.00 |
| No. 38 | 135 | 50 | 39 | 50 | 40 | 5.47 | 3.00 | 4.00 | 8.53 | 3.00 | 6.00 |
| No. 39 | 135 | 60 | 42 | 50 | 40 | 5.93 | 3.00 | 4.00 | 8.07 | 3.00 | 6.00 |
| No. 40 | 135 | 70 | 45 | 50 | 40 | 6.32 | 3.00 | 4.00 | 7.68 | 3.00 | 6.00 |

In some embodiments of the present disclosure, the method for generating a fertilizer formula based on the model for reduced fertilization of nitrogen, phosphorus, and potassium nutrients may also be used to guide fertilizer producers to produce fertilizers with different specifications, and the fertilizer producers may, in accordance with a user's needs, adjust a formulation of the fertilizers based on the model for reduced fertilization of nitrogen, phosphorus, and potassium nutrients through the processor directly, and directly produce a fertilizer that meets requirements of the above fertilization ratios and can be directly used by farmers.

At present, most of the fertilizer producers have mastered the production technology and processes of a special compounded fertilizer for the early rice and late rice. If adding film-coated controlled-release urea and conditioner to the special compound fertilizer, the nitrogen, phosphorus, and potassium nutrients may only be adjusted based on an original formula according to the model for reduced fertilization of nitrogen nutrient and the model for reduced fertilization of phosphorus and potassium nutrients. For example, a formula of the special compounded fertilizer for the early rice and late rice are 24–14–18 ($N$—$P_2O_5$—$K_2O$) and 28-14-18, respectively, and the reduced fertilization ratio of the phosphorus and potassium nutrients is 50% and 30%, respectively, according to a model for reduced fertilization of phosphorus and potassium nutrients for the early rice $T=0.91\ P+2.01K+7.71$ and a model for reduced fertilization of and phosphorus and potassium nutrients for the later rice $T=0.88\ P+2.05K+9$, according to a calculation result, the dosage of the conditioner for the early rice is 114 kg/mu, and the dosage of the conditioner for the late rice is 115 kg/mu, and then setting a mixing proportion of the film-coated controlled-release urea at 50%, according to $N=(-0.11\ T^2-0.08C^2+74.0C^2)$. $0.08C^2+74.75\ T+55.85C-0.35TC-4847.55)^{1/2}-(0.2\ T-0.41C+13.21)$, a calculation result shows that the reduced fertilization ratio of the nitro-gen nutrient for the early rice is 38%, and according to $N=(-0.13\ T^2-0.2C^2+47.9\ T+77.28C-0.21TC-4035)^{1/2}+(0.032\ T+0.038C-11.94)$, a calculation result shows that the reduced fertilization ratio of the nitrogen nutrient for the late rice is 37%. Then a formula for the early rice and late rice may be adjusted to 15–7–13 and 18–7–13 respectively. While producing fertilizers, producers may be completely in accordance with this formula, and at the same time in accordance with the early rice of 114 kg/mu, and late rice of 115 kg/mu dosage to mix the conditioner, which will not only reduce the enterprise production costs but also can significantly reduce the dosage of the nitrogen, phosphorus, potassium nutrients, significantly improving a utilization rate of fertilizer.

In some embodiments of the present disclosure, according to the method for generating a fertilizer formula based on the model for reduced fertilization of nitrogen, phosphorus, and potassium nutrients, rice producers or large-scale grain growers can conveniently and quickly adjust a fertilization dosage of the controlled-release fertilizer and the dosage of the conditioner, and can develop a reduced fertilization scheme tailored to an actual situation and reasonably design a ratio of the controlled-release fertilizer and a common fertilizer for rice while reducing fertilization and the dosage of the conditioner, which is simple and convenient to operate. The method not only can design a formula according to local conditions, but also improve the utilization rate of fertilizers, improve paddy soils, and also can significantly reduce input costs, reduce environmental pollution, and is especially suitable for long-term continuous use. In addition, the method has a good guiding role and reference value for fertilizer producers. Fertilizer producers can adjust their formulas according to the method, which not only can produce special fertilizers suitable for different climatic conditions and soil fertility levels but also can effectively reduce production costs.

It should be noted that the foregoing description of the process 300 is intended to be exemplary and illustrative only and does not limit the scope of application of the present disclosure. For a person skilled in the art, various corrections and changes can be made to the process 300 under the guidance of the present disclosure. However, these corrections and changes remain within the scope of the present disclosure.

One or more embodiments of the present disclosure provide a system for generating a fertilizer formula, including a processor, a storage unit, a monitoring device, and an Internet of Things unit communicatively connected to the processor.

The processor may be used to process information and/or data related to application scenarios of the system for generating a fertilizer formula. In some embodiments, the processor may process data, information, and/or results of processing obtained from other devices or components of a system and, based on such data, information, and/or results of processing, execute program instructions to perform one or more functions described in the present disclosure.

In some embodiments, the processor may obtain a basic formula for fertilization.

In some embodiments, the processor may obtain monitoring data based on the monitoring device and, based on the monitoring data, determine a soil feature of a predetermined point.

In some embodiments, the processor may obtain a phosphorus fertilizer price feature, a potassium fertilizer price feature, a soil feature, and a climatic feature from one or more Internet of Things units and determine a reduced fertilization ratio of a phosphorus nutrient and a reduced fertilization ratio of a potassium nutrient, and determine a dosage of a conditioner through a model for reduced fertilization of phosphorus and potassium nutrients.

In some embodiments, the processor may determine a fertilization ratio of a controlled-release fertilizer based on a controlled-release fertilizer price feature, the soil feature, and the climatic feature, and determine a reduced fertilization ratio of a nitrogen nutrient through a model for reduced fertilization of nitrogen nutrient and the dosage of the conditioner.

In some embodiments, the processor may determine the fertilizer formula based on the basic formula for fertilization, the reduced fertilization ratio of the phosphorus nutrient, the reduced fertilization ratio of the potassium nutrient, the dosage of the conditioner, the fertilization ratio of the controlled-release nitrogen fertilizer, and the reduced fertilization ratio of the nitrogen nutrient, and store the fertilizer formula in the storage unit.

The monitoring device may be a device for obtaining monitoring data. In some embodiments, the monitoring device may include a sensor, such as a temperature sensor, a humidity sensor, a pH sensor, or the like. In some embodiments, the monitoring device may be deployed at one or more predetermined points of a target planting unit.

The storage unit may store data, instructions, and/or any other information. In some embodiments, the storage unit may store the basic formula for fertilization, etc. The storage unit may include one or more storage components, each of which may be a stand-alone device or part of another device. In some embodiments, the storage unit may include random access memory (RAM), read-only memory (ROM), removable memory, etc., or any combination thereof. In some embodiments, the storage unit may be communicatively connected to the processor.

The Internet of Things unit is a basic constituent unit of the Internet of Things system, comprising a sensor and an actuator, and is capable of accomplishing data acquisition, processing, and transmission of the Internet of Things system. In some embodiments, the Internet of Things unit may acquire, process, and transmit the phosphorus fertilizer price feature, the potassium fertilizer price feature, the soil feature, and the climatic feature.

FIG. 4 is a flowchart illustrating an exemplary method for correcting a model for reduced fertilization of nitrogen, phosphorus, and potassium nutrients according to some embodiments of the present disclosure. In some embodiments, a process 400 may be executed by a processor. As shown in FIG. 4, the process 400 includes following steps.

Step 410, obtaining a basic formula for fertilization.

For a more detailed description of the basic formula for fertilization and a method of obtaining the basic formula, please see FIG. 1 and its related description.

Step 420, determining an optimized fertilization processing, a one-time fertilization processing, and a non-fertilization processing based on the basic formula for fertilization and a nutrient requirement law of rice.

In some embodiments, the processor may obtain, from a storage unit, the nutrient requirement law of rice pre-stored therein.

The optimized fertilization processing is to achieve the best fertilization effect by reasonably proportioning various nutrients according to factors such as a type of crop, a growth stage, and a soil condition during fertilization. The one-time fertilization processing refers to the one-time fertilization of various nutrient elements required at an early stage of crop growth, and no further fertilization later. The non-fertilization fertilization processing refers to that no fertilizer is fertilized during the crop growth, relying only on the soil's own fertility to meet requirements of the crop growth.

Step 430, obtaining optimized yield data (Y) of the optimized fertilization processing in an intelligent planting experiment, one-time yield data ($Y_0$) of the one-time fertilization processing, and corrected yield data ($Y_2$) of the non-fertilization fertilization processing when the model is corrected, and storing the optimized yield data (Y), the one-time yield data ($Y_1$), and the corrected yield data ($Y_2$) in the storage unit.

For a more detailed description of the intelligent planting experiment, please see FIG. 1 and its associated description.

In some embodiments, the processor may select experimental fields with different fertility as a target planting unit for the intelligent planting experiment.

For example, two experimental fields with different fertility were selected, experimental field I was located in Jinnan Village, Jinnan Town, Shanggao County, Jiangxi Province, with an experimental field area of 2 mu, soil being loam, and an organic matter content of 4.66%, which belonged to a field of higher fertility, and experimental field II was located in Xingguo Town, Xingguo County, Jiangxi Province, with an experimental field area of 1.6 mu, soil being sandy loam, and an organic matter content is 2.31%, which belongs to a field of lower fertility.

In some embodiments, both experimental field I and experimental field II conducted experiments on early rice and late rice, and there are three processings for each season of rice, such as the optimized fertilization processing, the one-time fertilization processing, and the non-fertilization processing, etc., with a fertilization dosage of nitrogen in optimized and one-time fertilization processings being 14 kg/mu, a fertilization dosage of phosphorus ($P_2O_5$) being 6 kg/mu, and a fertilization dosage of potassium ($K_2O$) being 10 kg/mu, of which a nitrogen fertilizer was used three times before transplanting, during tillering, and during spike differentiation period in the optimized fertilization processing, with a fertilization ratio of 2:1:1, and a phosphorus fertilizer and a potassium fertilizer were used all once before transplanting; and the one-time fertilization processing was to use the nitrogen fertilizer, the phosphorus fertilizer, and the potassium fertilizer all once before transplanting. Three replications were set up for each processing and arranged in randomized groups, and the daily field management was the same as the customary fertilization by local farmers.

The yield was measured when the rice was ripe, and a yield of the optimized fertilization processing (Y), a yield of the one-time fertilization processing ($Y_0$), and a yield of the non-fertilization processing ($Y_2$) were counted, and specific data are shown in Table 5 below.

TABLE 5

Technical Parameters Involved in Model Correction

| Type of model correction | Processing | Experimental field I | | Experimental field II | |
| --- | --- | --- | --- | --- | --- |
| | | Early rice (kg/mu) | Late rice (kg/mu) | Early rice (kg/mu) | Late rice (kg/mu) |
| A model for reduced fertilization of nitrogen nutrient | Optimized fertilization (Y) | 487 | 573 | 424 | 514 |
| | One-time fertilization ($Y_0$) | 426 | 497 | 351 | 421 |
| A model for reduced fertilization of phosphorus and potassium nutrient | Optimized fertilization (Y) | 487 | 573 | 424 | 514 |
| | Non-fertilization when the model is determined ($Y_1$) | 304 | 347 | 304 | 347 |
| | Non-fertilization when the model is corrected ($Y_2$) | 339 | 377 | 262 | 306 |

Step 440, determining a correction model for the model for reduced fertilization of nitrogen, phosphorus, and potassium nutrients through a correction algorithm, and storing the correction model in the storage unit based on the optimized yield data, the one-time yield data, the corrected yield data, and determined yield data of a non-fertilization processing when the model is determined.

In some embodiments, different types of rice correspond to different correction algorithms; in a correction equation for the model for reduced fertilization of phosphorus and potassium nutrients, a dosage of a conditioner is positively correlated to a reduced fertilization ratio of a phosphorus nutrient reduction ratio, a reduced fertilization ratio of a potassium nutrient, the optimized yield data, and the determined yield data, and the dosage of the conditioner is negatively correlated with the corrected yield data; and, in a correction equation for the model for reduced fertilization of nitrogen nutrient, a reduced fertilization ratio of a nitrogen nutrient is related to the dosage of the conditioner, a fertilization ratio of a controlled-release fertilizer, the optimized yield data, and the one-time yield data.

Exemplary Correction Algorithm:

A correction algorithm for reduced fertilization of phosphorus and potassium nutrients for early rice: T=0.91 P+2.01K+4.4 (Y−458.25+($Y_1$−$Y_2$)) ($R^2$=0.98, P=0.00084), and a correction algorithm for potassium nutrient reduction for late rice or middle rice: T=0.88 P+2.05K+3.72(Y−548.58+($Y_1$−$Y_2$)) ($R^2$=0.90, P=0.019).

A correction algorithm for reduced fertilization of nitrogen nutrient for early rice: N=(−0.11 $T^2$−0.08$C^2$+74.75 T+55.85C−0.35TC−75.41(Y−$Y_0$)+174.49)$^{1/2}$−(0.2 T−0.41C+13.21)($R^2$=0.98, P=0.0046).

A correction algorithm for reduced fertilization of nitrogen nutrient for late rice: N=(−0.13 $T^2$−0.2$C^2$+47.9 T+77.28C−0.21 TC−51.04(Y−$Y_0$)+142.56)$^{1/2}$+(0.032 T+0.038C−11.94) ($R^2$=0.98, P=0.0051).

In some embodiments, yield data of early rice and late rice obtained from the experimental field I and the experimental field II, and yield data ($Y_1$) obtained without fertilization processing when the model is determined are substituted into the above-mentioned correction algorithms, and a correction model is obtained by calculating as follows:

Correction models obtained for the experimental field I:

A correction model for reduced fertilization of phosphorus and potassium nutrients for early rice: T=0.91 P+2.01K−27.5 ($R^2$=0.98, P=0.00084);

A correction model for reduced fertilization of phosphorus and potassium nutrients for late rice: T=0.88 P+2.05K−20.76 ($R^2$=0.90, P=0.019);

A correction model for reduced fertilization of nitrogen nutrient for early rice: N=(−0.11 $T^2$−0.08$C^2$+74.75 T+55.85C−0.35TC−4400.63)$^{1/2}$−(0.2 T−0.41C+13.21) ($R^2$=0.98, P=0.0046);

A correction model for reduced fertilization of nitrogen nutrient for late rice: N=(−0.13 $T^2$−0.2$C^2$+47.9 T+77.28C−0.21TC−3737.24)$^{1/2}$+(0.032 T+0.038C−11.94) ($R^2$=0.98, P=0.0051).

Correction models obtained for the experimental field II:

A correction model for reduced fertilization of phosphorus and potassium nutrients for early rice: T=0.91 P+2.01K+34.1 ($R^2$=0.98, P=0.00084);

A correction model for reduced fertilization of phosphorus and potassium nutrients for late rice: T=0.88 P+2.05K+23.88 ($R^2$=0.90, P=0.019);

A correction model for reduced fertilization of nitrogen nutrient for early rice: N=(−0.11 $T^2$−0.08$C^2$+74.75 T+55.85C−0.35TC−5305.55)$^{1/2}$−(0.2 T−0.41C+13.21) ($R^2$=0.98, P=0.0046);

A correction model for reduced fertilization of nitrogen nutrient for late rice: N=(−0.13 $T^2$−0.2$C^2$+47.9 T+77.28C−0.21TC−4605.09)$^{1/2}$+(0.032 T+0.038C−11.94) ($R^2$=0.98, P=0.0051).

In some embodiments, yields are counted when rice of embodiments in the relevant description of FIG. 3 is ripe, and at the same time, samples plants are collected to determine a content of the nitrogen, phosphorus, and potassium nutrients in order to calculate a utilization ratio of the nitrogen, phosphorus, and potassium nutrients, and for specific data on rice yields and utilization ratios of the nitrogen, phosphorus, and potassium nutrients, please refer to Tables 6 and 7, and economic benefits are calculated, with specific results shown in Tables 8 and 9.

TABLE 6

Yield and utilization ratio of nutrients of early rice

| Experiment No. | Yield (kg/mu) | A utilization ratio of nutrients (%) | | |
|---|---|---|---|---|
| | | N | P | K |
| Optimized fertilization | 471 | 36.75 | 18.04 | 47.35 |
| No. 1 | 478 | 40.54 | 23.60 | 56.61 |
| No. 2 | 482 | 43.40 | 24.20 | 58.90 |
| No. 3 | 486 | 47.06 | 24.80 | 61.19 |
| No. 4 | 483 | 53.83 | 24.35 | 59.47 |
| No. 5 | 487 | 64.27 | 24.95 | 61.76 |
| No. 6 | 480 | 47.20 | 27.32 | 64.98 |
| No. 7 | 482 | 52.89 | 27.66 | 66.26 |
| No. 8 | 479 | 56.74 | 27.15 | 64.33 |
| No. 9 | 484 | 65.71 | 28.00 | 67.55 |
| No. 10 | 478 | 69.22 | 26.97 | 63.69 |
| No. 11 | 485 | 56.47 | 32.87 | 77.94 |
| No. 12 | 483 | 59.94 | 32.47 | 76.46 |
| No. 13 | 483 | 64.97 | 32.47 | 76.46 |
| No. 14 | 477 | 66.91 | 31.27 | 72.05 |
| No. 15 | 478 | 73.83 | 31.47 | 72.79 |
| No. 16 | 481 | 58.15 | 38.48 | 87.49 |
| No. 17 | 476 | 59.25 | 37.28 | 83.21 |
| No. 18 | 484 | 68.24 | 39.20 | 90.07 |
| No. 19 | 480 | 70.61 | 38.24 | 86.64 |
| No. 20 | 477 | 73.85 | 37.52 | 84.06 |

TABLE 7

Yield and utilization ratio of nutrients of late rice

| Experiment No. | Yield (kg/mu) | A utilization ratio of nutrients (%) | | |
|---|---|---|---|---|
| | | N | P | K |
| Optimized fertilization | 563 | 31.41 | 17.18 | 38.21 |
| No. 21 | 574 | 36.87 | 23.07 | 48.67 |
| No. 22 | 576 | 39.53 | 23.37 | 49.80 |
| No. 23 | 572 | 43.22 | 22.78 | 47.54 |
| No. 24 | 577 | 50.17 | 23.51 | 50.36 |
| No. 25 | 570 | 50.73 | 22.49 | 46.41 |
| No. 26 | 575 | 41.82 | 26.54 | 55.39 |
| No. 27 | 573 | 45.83 | 26.20 | 54.12 |
| No. 28 | 569 | 48.11 | 25.54 | 51.57 |
| No. 29 | 571 | 53.14 | 25.87 | 52.84 |
| No. 30 | 568 | 55.16 | 25.37 | 50.94 |
| No. 31 | 570 | 45.23 | 29.99 | 59.67 |
| No. 32 | 567 | 47.73 | 29.41 | 57.49 |
| No. 33 | 576 | 56.53 | 31.15 | 64.02 |
| No. 34 | 572 | 57.98 | 30.38 | 61.12 |
| No. 35 | 566 | 57.64 | 29.21 | 56.76 |
| No. 36 | 568 | 47.64 | 35.52 | 67.92 |
| No. 37 | 573 | 54.00 | 36.69 | 72.15 |
| No. 38 | 569 | 55.15 | 35.76 | 68.76 |
| No. 39 | 572 | 60.18 | 36.45 | 71.31 |
| No. 40 | 565 | 58.55 | 34.82 | 65.38 |

TABLE 8 calculation of economic benefits of early rice

| Experiment No. | Cost of fertilization | | | Yield benefits | | | |
|---|---|---|---|---|---|---|---|
| | Fertilizer (RMB/mu) | Labor (RMB/mu) | Total (RMB/mu) | Yield (kg/mu) | Unit price (RMB/kg) | Yield benefits (RMB/mu) | Production profits (RMB/mu) |
| Optimized fertilization | 210.76 | 75.00 | 285.76 | 471 | 2 | 942.00 | 656.24 |
| No. 1 | 233.42 | 25.00 | 258.42 | 478 | 2 | 956.00 | 697.58 |
| No. 2 | 234.76 | 25.00 | 259.76 | 482 | 2 | 964.00 | 704.24 |
| No. 3 | 234.42 | 25.00 | 259.42 | 486 | 2 | 972.00 | 712.58 |
| No. 4 | 222.35 | 25.00 | 247.35 | 483 | 2 | 966.00 | 718.65 |
| No. 5 | 213.11 | 25.00 | 238.11 | 487 | 2 | 974.00 | 735.89 |
| No. 6 | 226.08 | 25.00 | 251.08 | 480 | 2 | 960.00 | 708.92 |
| No. 7 | 221.46 | 25.00 | 246.46 | 482 | 2 | 964.00 | 717.54 |
| No. 8 | 216.73 | 25.00 | 241.73 | 479 | 2 | 958.00 | 716.27 |
| No. 9 | 211.84 | 25.00 | 236.84 | 484 | 2 | 968.00 | 731.16 |
| No. 10 | 206.73 | 25.00 | 231.73 | 478 | 2 | 956.00 | 724.27 |
| No. 11 | 220.33 | 25.00 | 245.33 | 485 | 2 | 970.00 | 724.67 |
| No. 12 | 217.70 | 25.00 | 242.70 | 483 | 2 | 966.00 | 723.30 |
| No. 13 | 214.76 | 25.00 | 239.76 | 483 | 2 | 966.00 | 726.24 |
| No. 14 | 211.53 | 25.00 | 236.53 | 477 | 2 | 954.00 | 717.47 |
| No. 15 | 208.02 | 25.00 | 233.02 | 478 | 2 | 956.00 | 722.98 |
| No. 16 | 221.09 | 25.00 | 246.09 | 481 | 2 | 962.00 | 715.91 |
| No. 17 | 219.50 | 25.00 | 244.50 | 476 | 2 | 952.00 | 707.50 |
| No. 18 | 217.64 | 25.00 | 242.64 | 484 | 2 | 968.00 | 725.36 |
| No. 19 | 215.53 | 25.00 | 240.53 | 480 | 2 | 960.00 | 719.47 |
| No. 20 | 213.20 | 25.00 | 238.20 | 477 | 2 | 954.00 | 715.80 |

TABLE 9 calculation of economic benefits of late rice

| | Cost of fertilization | | | Yield benefits | | | |
| | | | | | | Yield | Production |
| Experiment No. | Fertilizer (RMB/mu) | Labor (RMB/mu) | Total (RMB/mu) | Yield (kg/mu) | Unit price (RMB/kg) | benefits (RMB/mu) | profits (RMB/mu) |
|---|---|---|---|---|---|---|---|
| Optimized fertilization | 226.41 | 75.00 | 301.41 | 563 | 2.4 | 1351.20 | 1049.79 |
| No. 21 | 250.36 | 25.00 | 275.36 | 574 | 2.4 | 1377.60 | 1102.24 |
| No. 22 | 249.69 | 25.00 | 274.69 | 576 | 2.4 | 1382.40 | 1107.71 |
| No. 23 | 239.52 | 25.00 | 264.52 | 572 | 2.4 | 1372.80 | 1108.28 |
| No. 24 | 233.31 | 25.00 | 258.31 | 577 | 2.4 | 1384.80 | 1126.49 |
| No. 25 | 228.79 | 25.00 | 253.79 | 570 | 2.4 | 1368.00 | 1114.21 |
| No. 26 | 242.94 | 25.00 | 267.94 | 575 | 2.4 | 1380.00 | 1112.06 |
| No. 27 | 235.83 | 25.00 | 260.83 | 573 | 2.4 | 1375.20 | 1114.37 |
| No. 28 | 231.05 | 25.00 | 256.05 | 569 | 2.4 | 1365.60 | 1109.55 |
| No. 29 | 227.48 | 25.00 | 252.48 | 571 | 2.4 | 1370.40 | 1117.92 |
| No. 30 | 224.69 | 25.00 | 249.69 | 568 | 2.4 | 1363.20 | 1113.51 |
| No. 31 | 235.60 | 25.00 | 260.60 | 570 | 2.4 | 1368.00 | 1107.40 |
| No. 32 | 231.68 | 25.00 | 256.68 | 567 | 2.4 | 1360.80 | 1104.12 |
| No. 33 | 228.76 | 25.00 | 253.76 | 576 | 2.4 | 1382.40 | 1128.64 |
| No. 34 | 226.53 | 25.00 | 251.53 | 572 | 2.4 | 1372.80 | 1121.27 |
| No. 35 | 224.84 | 25.00 | 249.84 | 566 | 2.4 | 1358.40 | 1108.56 |
| No. 36 | 234.77 | 25.00 | 259.77 | 568 | 2.4 | 1363.20 | 1103.43 |
| No. 37 | 232.32 | 25.00 | 257.32 | 573 | 2.4 | 1375.20 | 1117.88 |
| No. 38 | 230.54 | 25.00 | 255.54 | 569 | 2.4 | 1365.60 | 1110.06 |
| No. 39 | 229.28 | 25.00 | 254.28 | 572 | 2.4 | 1372.80 | 1118.52 |
| No. 40 | 228.50 | 25.00 | 253.50 | 565 | 2.4 | 1356.00 | 1102.50 |

As can be seen from data in Tables 6–9, using a fertilization scheme determined in some embodiments of the present disclosure not only reduces fertilizes without reducing yields, but also improves the utilization rate of the nitrogen, phosphorus, and potassium nutrients, which reduces the production cost of producers and increases the economic benefits of rice.

Some embodiments of the present disclosure also provide the method for correcting a model for reduced fertilization of nitrogen, phosphorus, and potassium nutrients, which is capable of timely adjusting the model in the event of parameter changes (e.g., soil fertility, climatic conditions, and cultivation and management techniques), so as to ensure that the model has accurate guidance and reference value for the actual production, and the method for correcting the model is very simple, which can correct the model by designing three processing including the non-fertilization, the one-time fertilization and the optimized fertilization.

One or more embodiments of the present disclosure provide a system for correcting a model for reduced fertilization of nitrogen, phosphorus, and potassium nutrients, comprising a processor, a storage unit communicatively connected to the processor, and a monitoring device.

The processor may be used to process information and/or data related to application scenarios of a system for generating a fertilizer formula. In some embodiments, the processor may process data, information, and/or results of processing obtained from other devices or components of a system and, based on such data, information, and/or results of processing, execute program instructions to perform one or more functions described in the present disclosure.

In some embodiments, the processor may obtain a basic formula for fertilization.

In some embodiments, the processor may determine an optimized fertilization processing, a one-time fertilization processing, and a non-fertilization processing based on the basic formula for fertilization and a nutrient requirement law of rice.

In some embodiments, the processor may obtain optimized yield data of the optimized fertilization processing in an intelligent planting experiment, one-time yield data of the one-time fertilization processing, and corrected yield data of the non-fertilization processing when the model is corrected and store the optimized yield data, the one-time yield data, and the corrected yield data in the storage unit.

In some embodiments, the processor may determine a correction model for the model for reduced fertilization of nitrogen, phosphorus, and potassium nutrients based on the optimized yield data, the one-time yield data, the corrected yield data, and determined yield data without fertilization processing when the model is determined through a correction algorithm, and store the correction model stored in the storage unit.

The monitoring device may be a device for obtaining monitoring data. In some embodiments, the monitoring device may include a sensor, such as a temperature sensor, a humidity sensor, a pH sensor, or the like. In some embodiments, the monitoring device may be deployed at one or more predetermined points of a target planting unit.

The storage unit may store data, instructions, and/or any other information. In some embodiments, the storage unit may store the nutrient requirement law of rice, the correction model, or the like. The storage unit may include one or more storage components, each of which may be a stand-alone device or part of another device. In some embodiments, the storage unit may include random access memory (RAM), read-only memory (ROM), removable memory, etc., or any combination thereof. In some embodiments, the storage unit may be communicatively connected to the processor.

In some embodiments, a validation of a method for correction of FIG. 4 and its description is carried out, and designing a fertilizer formula using a correction model obtained by the method for correction of FIG. 4 and its description, and a design manner is the same as that of FIG. 3 and its description of a method for generating a fertilizer formula, and results are shown in Tables 10 to Table 13:

TABLE 10

Fertilization formula and yields of early rice in the experimental field I

| | Dosage of conditioner (kg/mu) | Fertilization ratio of a controlled-release urea (%) | Reduced fertilization ratio of nutrients (%) | | | Reduced dosage of nutrients (kg/mu) | | | Actual dosage of nutrients used (kg/mu) | | | Yield (kg/mu) |
|---|---|---|---|---|---|---|---|---|---|---|---|---|
| | | | N | P₂O₅ | K₂O | N | P₂O₅ | K₂O | N | P₂O₅ | K₂O | |
| Optimized fertilization | 0 | 0 | 0 | 0 | 0 | 0 | 0 | 0 | 12 | 6 | 10 | 476 |
| Test No. 1 | 40 | 30 | 9 | 30 | 20 | 1.08 | 1.80 | 2.00 | 10.92 | 4.20 | 8.00 | 475 |
| Test No. 2 | 69 | 50 | 34 | 40 | 30 | 4.05 | 2.40 | 3.00 | 7.95 | 3.60 | 7.00 | 483 |
| Test No. 3 | 98 | 70 | 51 | 50 | 40 | 6.07 | 3.00 | 4.00 | 5.93 | 3.00 | 6.00 | 479 |

TABLE 11

Fertilization formula and yields of middle rice and late rice in the experimental field I

| | Dosage of conditioner (kg/mu) | Fertilization ratio of a controlled-release urea (%) | Reduced fertilization ratio of nutrients (%) | | | Reduced fertilization dosage of nutrients (kg/mu) | | | Actual dosage of nutrients used (kg/mu) | | | Yield (kg/mu) |
|---|---|---|---|---|---|---|---|---|---|---|---|---|
| | | | N | P₂O₅ | K₂O | N | P₂O₅ | K₂O | N | P₂O₅ | K₂O | |
| Optimized fertilization | 0 | 0 | 0 | 0 | 0 | 0 | 0 | 0 | 14 | 6 | 10 | 581 |
| Test No. 4 | 47 | 30 | 5 | 30 | 20 | 0.70 | 1.80 | 2.00 | 13.30 | 4.20 | 8.00 | 585 |
| Test No. 5 | 76 | 50 | 34 | 40 | 30 | 4.74 | 2.40 | 3.00 | 9.26 | 3.60 | 7.00 | 588 |
| Test No. 6 | 105 | 70 | 46 | 50 | 40 | 6.51 | 3.00 | 4.00 | 7.49 | 3.00 | 6.00 | 579 |

TABLE 12

Fertilization formula and yields of early rice in the experimental field II

| | Dosage of conditioner (kg/mu) | Fertilization ratio of a controlled-release urea (%) | Reduced fertilization ratio of nutrients (%) | | | Reduced fertilization dosage of nutrients (kg/mu) | | | Actual dosage of nutrients used (kg/mu) | | | Yield (kg/mu) |
|---|---|---|---|---|---|---|---|---|---|---|---|---|
| | | | N | P₂O₅ | K₂O | N | P₂O₅ | K₂O | N | P₂O₅ | K₂O | |
| Optimized fertilization | 0 | 0 | 0 | 0 | 0 | 0 | 0 | 0 | 12 | 6 | 10 | 476 |
| Test No. | 40 | 30 | 9 | 30 | 20 | 1.08 | 1.80 | 2.00 | 10.92 | 4.20 | 8.00 | 475 |
| Test No. 2 | 69 | 50 | 34 | 40 | 30 | 4.05 | 2.40 | 3.00 | 7.95 | 3.60 | 7.00 | 483 |
| Test No. 3 | 98 | 70 | 51 | 50 | 40 | 6.07 | 3.00 | 4.00 | 5.93 | 3.00 | 6.00 | 479 |
| Optimized fertilization | 0 | 0 | 0 | 0 | 0 | 0 | 0 | 0 | 12 | 6 | 10 | 411 |
| Test No. 7 | 102 | 30 | 20 | 30 | 20 | 2.39 | 1.80 | 2.00 | 9.61 | 4.20 | 8.00 | 404 |
| Test No. 8 | 131 | 50 | 35 | 40 | 30 | 4.19 | 2.40 | 3.00 | 7.81 | 3.60 | 7.00 | 416 |
| Test No. 9 | 160 | 70 | 42 | 50 | 40 | 5.05 | 3.00 | 4.00 | 6.95 | 3.00 | 6.00 | 414 |

TABLE 13

Fertilization formula and yields of middle rice and late rice in the experimental field II

| | Dosage of conditioner (kg/mu) | Fertilization ratio of a controlled-release urea (%) | Reduced fertilization ratio of nutrients (%) | | | Reduced fertilization dosage of nutrients (kg/mu) | | | An actual dosage of nutrients used (kg/mu) | | | Yield (kg/mu) |
|---|---|---|---|---|---|---|---|---|---|---|---|---|
| | | | N | P₂O₅ | K₂O | N | P₂O₅ | K₂O | N | P₂O₅ | K₂O | |
| Optimized fertilization | 0 | 0 | 0 | 0 | 0 | 0 | 0 | 0 | 14 | 6 | 10 | 509 |
| Test No. 10 | 91 | 30 | 8 | 30 | 20 | 1.10 | 1.80 | 2.00 | 12.90 | 4.20 | 8.00 | 515 |

TABLE 13-continued

| | | | | | | | | | | | | |
|---|---|---|---|---|---|---|---|---|---|---|---|---|
| | | Fertilization formula and yields of middle rice and late rice in the experimental field II | | | | | | | | | | |
| | Dosage of condi- tioner | Fertili- zation ratio of a controlled- release urea | Reduced fertilization ratio of nutrients (%) | | | Reduced fertilization dosage of nutrients (kg/mu) | | | An actual dosage of nutrients used (kg/mu) | | | Yield |
| | (kg/mu) | (%) | N | P₂O₅ | K₂O | N | P₂O₅ | K₂O | N | P₂O₅ | K₂O | (kg/mu) |
| Test No. 11 | 121 | 50 | 31 | 40 | 30 | 4.33 | 2.40 | 3.00 | 9.67 | 3.60 | 7.00 | 511 |
| Test NO.12 | 150 | 70 | 39 | 50 | 40 | 5.44 | 3.00 | 4.00 | 8.56 | 3.00 | 6.00 | 517 |

As can be seen from Tables 10 to Table 13 above, the fertilizer formula designed in accordance with the correction model obtained from FIG. 4 and the method for correction as described are able to reduce fertilizers without reducing yields.

In some embodiments, the method for determining a model for reduced fertilization of nitrogen, phosphorus, and potassium nutrients may further include following steps:

S11: determining a basic formula for fertilization for rice.

In some embodiments, determining the basic formula for fertilization for rice may also be referred to as obtaining a basic formula for fertilization. For a more detailed description of obtaining the basic formula for fertilization, please see FIG. 1 and its related description.

S12: designing an experimental processing using methods such as a uniform experimental design and an orthogonal experimental design, and designing an optimized fertilization processing as a control.

For more description of the uniform experimental designs, the orthogonal experimental designs, the experimental processing, and the optimized fertilization processing, reference may be made to FIG. 1 and its related description.

S13: Calculating a fertilization dosage, based on a dosage of a conditioner, a fertilization ratio of a controlled-release fertilizer, and a reduced fertilization ratio of nitrogen, phosphorus, and potassium nutrients in an experimental processing in step S12, and the basic formula for fertilization determined in step S11, calculating a corresponding fertilization dosage.

More description on calculating the corresponding fertilization dosage based on the dosage of the conditioner, the fertilization ratio of the controlled-release fertilizer, and the reduced fertilization ratio of the nitrogen, phosphorus, and potassium nutrients can be found in FIG. 1 and its related description.

S14: determining the model for reduced fertilization of nitrogen, phosphorus, and potassium nutrients; conducting a field planting experiment in accordance with the experimental processing designed in step S12 and the fertilization dosage obtained in step S13, counting a rice yield of each experimental processing and the optimized fertilization processing, and then fitting each experimental processing using a regression model to obtain a mathematical equation, substituting rice yield data of the optimized fertilization processing into the equation, and obtaining the model for reduced fertilization of nitrogen, phosphorus, and potassium nutrients. The model for reduced fertilization of phosphorus, phosphorus, and potassium nutrients includes a model for reduced fertilization of phosphorus and potassium nutrients and a model for reduced fertilization of nitrogen nutrient.

In some embodiments, the field planting experiment may also be referred to as an intelligent planting experiment.

For a more detailed description of the intelligent planting experiment, the rice yields, the regression model, and how the model for reduced fertilization of nitrogen, phosphorus, and potassium nutrients was determined, please see FIG. 1 and its related description.

In some embodiments, in step S12, designing the experimental processing comprises: without reducing the nitrogen nutrient and without fertilizing the controlled-release nitrogen fertilizer, taking the conditioner, phosphorus nutrient, and potassium nutrient as three experimental factors, and using the dosage of the conditioner and the reduced fertilization ratio of the phosphorus and potassium nutrients as an experimental level, obtaining a first set of experimental processings by using the uniform experimental design and designing the optimized fertilization processing as a control; and, without reducing the phosphorus and potassium nutrients, using the conditioner, the controlled-release nitrogen fertilizer, and the nitrogen nutrient as three experimental factors, and using the dosage of the conditioner, the fertilization ratio of the controlled-release nitrogen fertilizer, and the reduced fertilization ratio of the nitrogen nutrient as an experimental level, using "3414", L16 (43) or L25 (53) orthogonal experimental design to obtain a second set of experimental processings, and designing the optimized fertilization processing as a control.

The experimental level is to set a dosage level according to an experimental design within a dosage range of the conditioner, to set a fertilization ratio level according to an experimental design with a fertilization ratio level of the controlled-release nitrogen fertilizer, and to set a reduced fertilization ratio level according to an experimental design within a reduced fertilization ratio range of the nitrogen, phosphorus, and potassium nutrients; wherein the dosage range of the conditioner ranges from 0–250 kg/mu, the fertilization ratio range of the controlled-release nitrogen fertilizer ranges from 0%-85%, and the reduced fertilization ratio range of the nitrogen, phosphorus, and potassium nutrients ranges from 0%-50%, 0%-65%, and 0%-50%, respectively.

In some embodiments, the first/second set of experimental processings may also be referred to as a first/second experimental scheme, and more description of the first/second experimental scheme may be found in FIG. 1 and its related description.

In some embodiments, step S14 includes: conducting a rice field planting experiment based on the first set of experimental processing and the optimized fertilization processing, counting a rice yield of each experimental processing, and then fitting a dosage of the conditioner, and reduced fertilization ratio data of the phosphorus and potassium nutrients and rice yield data obtained of each experimental processing using a regression model to obtain a mathematical equation between the dosage of the conditioner, the reduced fertilization ratio of the phosphorus and potassium nutrients and the yield, and substituting rice yield data of the optimized fertilization processing into the equation to obtain a mathematical model of a functional relationship between the dosage of the conditioner and reduced fertilization ratio of the phosphorus and potassium nutrients, i.e., the model for reduced fertilization of phosphorus and potassium nutrients; and, conducting a rice field planting experiment based on the second set of experimental processings and optimized fertilization processing, counting a rice yield of each experimental processing, and then fitting a dosage of the conditioner, fertilization ratio data of a controlled-release urea, and reduced fertilization ratio data of the nitrogen nutrient and yield data obtained from each experimental processing using a regression model to obtain a mathematical equation between the dosage of the conditioner, the fertilization ratio of the controlled-release urea, the reduced fertilization ratio of the nitrogen nutrient, and the rice yield, substituting the rice yield data of the optimized fertilization processing into the equation to obtain a mathematical model of a functional relationship between the reduced fertilization ratio of the nitrogen nutrient and the fertilization ratio of the controlled-release nitrogen fertilizer, i.e., the model for reduced fertilization of nitrogen nutrient.

In some embodiments, the rice yield of the experimental processing may be referred to as experimental yield data, and the rice yield data of the optimized fertilization processing may be referred to as optimized yield data.

For more description of the experimental yield data, fitting with the regression model, and the determination of the model for reduced fertilization of nitrogen nutrient and the model for reduced fertilization of phosphorus and potassium nutrients, please see FIG. 1 and its related description.

In some embodiments, the optimized fertilization processing is fertilization using soil testing formulation fertilization technology; wherein the nitrogen fertilizer is used in three times as basic fertilizer, tiller fertilizer, and spike fertilizer, respectively, and the phosphorus fertilizer and potassium fertilizer are used all once as basic fertilizer.

In some embodiments, in step S11, determining the basic formula for fertilization for rice comprises determining a type of rice, the type of rice being early rice, middle rice, or late rice.

In some embodiments, the model for reduced fertilization of phosphorus and potassium nutrients comprises: a model for reduced fertilization of phosphorus and potassium nutrients for early rice: $T=0.91 \, P+2.01K+7.71$; and, a model for reduced fertilization of phosphorus and potassium nutrients for middle rice or late rice: $T=0.88 \, P+2.05K+9$; wherein T is the dosage of the conditioner, P is the reduced fertilization ratio of the phosphorus nutrient, and K is the reduced fertilization ratio of the potassium nutrient, $P \leq 65\%$ and $K \leq 50\%$; and the model for reduced fertilization of nitrogen nutrient includes: a model for reduced fertilization of nitrogen nutrient for early rice: $N=(-0.11 \, T^2-0.08C^2+74.75 \, T+55.85C-0.35TC-4847.55)^{1/2}-(0.2 \, T-0.41C+13.21)$; and, a model for reduced fertilization of nitrogen nutrient for middle rice or late rice: $N=(-0.13 \, T^2-0.2C^2+47.9 \, T+77.28C-0.21TC-4035)^{1/2}+(0.032 \quad T+0.038C-11.94)$; wherein N is the reduced fertilization ratio of the nitrogen nutrient, T is the dosage of the conditioner, and C is the fertilization ratio of the controlled-release nitrogen fertilizer, $40 \leq T \leq 250$ kg/mu, $20\% \leq C \leq 85\%$.

In some embodiments, a method for designing a fertilizer formula includes following steps:

S21: determining a basic formula for fertilization for rice.

For more instructions on the basic formula for fertilization for rice, see the related description above.

S22: setting a reduced fertilization ratio of the phosphorus and potassium nutrients based on the cost-effectiveness of phosphorus and potassium fertilizers and local soil and climatic condition, and obtaining a dosage of a conditioner through a model for reduced fertilization of phosphorus and potassium nutrients.

In some embodiments, the cost-effectiveness of the phosphorus and potassium fertilizers may be referred to as a phosphorus and potassium price feature; the local soil may be referred to as a soil feature; the climatic condition may be referred to as a climatic feature; and the reduced fertilization ratio of the phosphorus and potassium nutrients may be referred to as a reduced fertilization ratio of phosphorus and potassium, and more descriptions can be found in FIG. 3 and its related descriptions.

S23: setting a fertilization ratio of a controlled-release fertilizer based on the cost-effectiveness of the controlled-release fertilizer and the local soil and climatic condition, and calculating based on a model for reduced fertilization of nitrogen nutrient and a dosage of a conditioner determined in step S22 to obtain a reduced fertilization ratio of the nitrogen nutrient.

For more instructions on setting the fertilization ratio of the controlled-release fertilizer, and calculating the reduced fertilization ratio of the nitrogen nutrient, see FIG. 3 and its related description.

S24: Based on the basic formula for fertilization determined in step S21, the reduced fertilization ratio of the phosphorus and potassium nutrients, the dosage of the conditioner determined in step S22, and the fertilization ratio of the controlled-release nitrogen fertilizer, and the reduced fertilization ratio of the nitrogen nutrient in step S23, calculating to obtain the fertilizer formula, and a reduced fertilization model is obtained by a method for determining the model for reduced fertilization of nitrogen, phosphorus, and potassium nutrients.

For a more detailed description of calculating to obtain the fertilizer formula, please see FIG. 3 and its related description.

In some embodiments, in the method for designing the fertilizer formula, the controlled-release nitrogen fertilizer is resin-coated urea; and the basic formula for fertilization for rice includes a basic formula for fertilization for early rice and a basic formula for fertilization for late rice or middle rice. The basic formula for fertilization for the early rice is that a fertilization dosage of pure nitrogen (N) is 10–15 kg/mu, a fertilization dosage of pure phosphorus ($P_2O_5$) is 5–8 kg/mu, and a fertilization dosage of pure potassium ($K_2O$) is 8–12 kg/mu; and the basic formula for fertilization for late or middle rice is a fertilization dosage of pure nitrogen (N) is 12–18 kg/mu, a fertilization dosage of pure phosphorus ($P_2O_5$) is 5–8 kg/mu, and a fertilization dosage of pure potassium ($K_2O$) is 8–12 kg/mu. A controlled-release period of a controlled-release nitrogen fertilizer selected for the early rice is 50–75 days, and a controlled-release period of a controlled-release nitrogen fertilizer selected for the late rice or middle rice is 70–105 days.

In some embodiments, the model for reduced fertilization of nitrogen, phosphorus, and potassium nutrients is obtained by a method for determining the model for reduced fertilization of nitrogen, phosphorus, and potassium nutrients, and a method for correcting the model for reduced fertilization of nitrogen, phosphorus, and potassium nutrients comprises following steps:

S31: determining a basic formula for fertilization for rice.

For more instructions on the basic formula for fertilization for rice, see the related description above.

S32: setting an optimized fertilization processing, one-time fertilization processing, and non-fertilization processing according to the basic formula for fertilization for rice and a nutrient requirement law of rice.

In some embodiments, for more information about the optimized fertilization processing, the one-time fertilization processing, and the non-fertilization processing, please refer to FIG. 4 and its associated description.

S33: conducting a field planting experiment and counting a yield of the optimized fertilizer processing, a yield of the one-time fertilization processing, and a yield of the non-fertilization processing when the model is corrected.

In some embodiments, the yield of the optimized fertilization processing, the yield of the one-time fertilization processing, and the yield of the non-fertilization processing when the model is corrected may be referred to as optimized yield data, one-time yield data, and corrected yield data, respectively, and more descriptions may be found in FIG. 4 and its related description.

S34: substituting the yield of the optimized fertilization processing, the yield of the one-time fertilization processing, and the yield of the non-fertilization processing when the model is determined, and the yield of the non-fertilization processing when the model is corrected obtained at step S33 into a correction equation to obtain a correction model of the model for reduced fertilization of nitrogen, phosphorus, and potassium nutrients.

In some embodiments, the yield data of the non-fertilization processing when the model is determined may be referred to as determined yield data, and the correction equation may be referred to as a correction algorithm, and a further description may be found in FIG. 4 and its related notes.

In some embodiments, the correction equation may include: a correction equation of a model for reduced fertilization of phosphorus and potassium nutrients for early rice: $T=0.91\ P+2.01K+4.4\ (Y-458.25+(Y1-Y2))$, wherein T is a dosage of a conditioner, P is a reduced fertilization ratio of phosphorus ($P\le65\%$), K is a reduced fertilization ratio of potassium ($K\le50\%$), Y is the yield data of the optimized fertilization processing, $Y_1$ is the yield of the non-fertilization processing when the model is determined, and $Y_2$ is the yield of the non-fertilization processing when the model is corrected; and a correction equation of a model for reduced fertilization of phosphorus and potassium nutrients for late rice or middle rice: $T=0.88\ P+2.05K+3.72\ (Y-548.58+(Y_1-Y_2))$; a correction equation of a model for reduced fertilization of nitrogen nutrient for early rice: $N=(-0.11\ T^2-0.08C^2+74.75\ T+55.85C-0.35TC-75.41(Y-Y_0)+174.49)^{1/2}-(0.2\ T-0.41C+13.21)$, in the formula, N is the reduced fertilization ratio of nitrogen, T is the dosage of the conditioner, C is the fertilization ratio of the controlled-release fertilizer, Y is the yield data of the optimized fertilization processing, and $Y_0$ is the yield of the one-time fertilization processing; and the correction equation of the model for reduced fertilization of nitrogen nutrient for late rice or middle rice: $N=(-0.13\ T^2-0.2C^2+47.9\ T+77.28C-0.21TC-51.04(Y-Y_0)+142.56)^{1/2}+(0.032\ T+0.038C-11.94)$.

The basic concepts have been described above, and it is apparent to those skilled in the art that the foregoing detailed disclosure is intended as an example only and does not constitute a limitation of the present disclosure. While not expressly stated herein, various modifications, improvements, and amendments may be made to the present disclosure by those skilled in the art. Those types of modifications, improvements, and amendments are suggested in the present disclosure, so those types of modifications, improvements, and amendments remain within the spirit and scope of the exemplary embodiments of the present disclosure.

Also, the present disclosure uses specific words to describe embodiments of the present disclosure. such as "an embodiment", "one embodiment", and/or "some embodiment" means a feature, structure, or characteristic associated with at least one embodiment of the present disclosure. Accordingly, it should be emphasized and noted that "an embodiment", "one embodiment" or "an alternative embodiment" referred to two or more times in different places in the present disclosure do not necessarily refer to the same embodiment. In addition, certain features, structures, or characteristics in one or more embodiments of the present disclosure may be suitably combined.

Additionally, unless expressly stated in the claims, the order of the processing elements and sequences, the use of numerical letters, or the use of other names as described in the present disclosure are not intended to qualify the order of the processes and methods of the present disclosure. While some embodiments of the present disclosure that are currently considered useful are discussed in the foregoing disclosure by way of various examples, it should be appreciated that such details serve only illustrative purposes and that additional claims are not limited to the disclosed embodiments, rather, the claims are intended to cover all amendments and equivalent combinations that are consistent with the substance and scope of the embodiments of the present disclosure. For example, although the implementation of various components described above may be embodied in a hardware device, it may also be implemented as a software only solution, e.g., an installation on an existing server or mobile device.

Similarly, it should be noted that in order to simplify the presentation of the disclosure of the present disclosure, and thereby aid in the understanding of one or more embodiments of the invention, the foregoing descriptions of embodiments of the present disclosure sometimes group multiple features together in a single embodiment, accompanying drawings, or in a description thereof. However, this method of disclosure does not imply that the objects of the present disclosure require more features than those mentioned in the claims. Rather, claimed subject matter may lie in less than all features of a single foregoing disclosed embodiment.

Numbers describing the number of components, attributes, and properties are used in some embodiments, and it is to be understood that such numbers used in the description of embodiments are modified in some examples by the modifiers "about", "approximately", or "roughly". Unless otherwise noted, the terms "about," "approximately," or "roughly" indicates that a ±20% variation in the stated number is allowed. Correspondingly, in some embodiments, the numerical parameters used in the present disclosure and claims are approximations, which can change depending on the desired characteristics of the individual embodiment. In some embodiments, the numerical parameters should take into account the specified number of valid digits and employ general place-keeping. While the numerical domains and parameters used to confirm the breadth of their ranges in some embodiments the present disclosure are approximations, in specific embodiments, such values are set to be as precise as possible within a feasible range.

For each patent, patent application, patent application disclosure, and other material cited in the present disclosure, such as articles, books, specification sheets, publications, documents, etc., the entire contents of which are hereby incorporated herein by reference. Historical application documents that are inconsistent with or create a conflict with the contents of the present disclosure are excluded, as well as documents that limit the broadest scope of the claims of the present disclosure (currently or hereafter appended to the present disclosure). It should be noted that in the event of any inconsistency or conflict between the descriptions, definitions, and/or use of terminology in the materials appended to the present disclosure and those set forth in the present disclosure, the descriptions, definitions, and/or use of terms in the present disclosure shall prevail.

Finally, it should be understood that the embodiments described in the present disclosure are used only to illustrate the principles of the embodiments of the present disclosure. Other deformations may also fall within the scope of the present disclosure. As such, alternative configurations of embodiments of the present disclosure may be viewed as consistent with the teachings of the present disclosure as an example, not as a limitation. Correspondingly, the embodiments of the present disclosure are not limited to the embodiments expressly presented and described herein.

What is claimed is:

1. A method for generating a fertilizer formula, wherein the method is executed by a processor, comprising:

obtaining a basic formula for fertilization;

obtaining monitoring data based on a monitoring device, the monitoring device being deployed at a predetermined point of a target planting unit;

determining a soil feature of the predetermined point based on the monitoring data;

determining an experimental scheme and experimental parameters based on the soil feature and an experimental design, and the experimental scheme comprising one or more experimental processings and an optimized fertilization processing as a control, the experimental parameters comprising a dosage of a conditioner, a fertilization ratio of a controlled-release fertilizer, a reduced fertilization ratio of a nitrogen nutrient, a reduced fertilization ratio of a phosphorus nutrient, and a reduced fertilization ratio of a potassium nutrient;

determining a fertilization dosage based on the experimental parameters and the basic formula for fertilization, and conducting an intelligent planting experiment based on the fertilization dosage and the experimental scheme; wherein the intelligent planting experiment comprises:

obtaining a physicochemical feature at one or more time points corresponding to a predetermined sub-region of the target planting unit based on the monitoring device and compressing and storing the physicochemical feature within a predetermined compression intensity to obtain a physicochemical feature sequence of the predetermined sub-region, the physicochemical feature comprising at least one of a temperature, a humidity, a pH value, or an EC value, and the predetermined compression intensity being determined based on a residual storage capacity of a storage unit;

determining whether an abnormal sub-region exists based on the physicochemical feature sequence; and in response to a determination that the abnormal sub-region exists, performing a predetermined processing on the abnormal sub-region;

wherein the monitoring device collects the physicochemical feature at a first collection frequency and uploads the physicochemical feature to the processor, the first collection frequency is issued by the processor to the monitoring device within a first predetermined period, the first collection frequency is determined based on a free resource bandwidth of the processor in a future time period, and the first predetermined period is determined based on a change rate of a free resource bandwidth of the processor in a historical time period;

obtaining experimental parameters and experimental yield data of each of the one or more experimental processings, and optimized yield data of the optimized fertilization processing, and storing the experimental parameters, the experimental yield data, and the optimized yield data in the storage unit; and determining a model for reduced fertilization of nitrogen, phosphorus, and potassium nutrients based the experimental parameters, the experimental yield data, and the optimized yield data through a regression model, and storing the model for reduced fertilization of nitrogen, phosphorus, and potassium nutrients in the storage unit, wherein the regression model is extracted by the processor from the storage unit, and the model for reduced fertilization of nitrogen, phosphorus, and potassium nutrients comprises a model for reduced fertilization of phosphorus and potassium nutrients and a model for reduced fertilization of nitrogen nutrient.

2. The method according to claim 1, wherein the experimental scheme is determined based on a uniform experimental design and an orthogonal experimental design, comprising:

without reducing the nitrogen nutrient and without fertilizing a controlled-release nitrogen fertilizer, using the conditioner, the phosphorus nutrient, and the potassium nutrient as three experimental factors, and using the dosage of the conditioner, the reduced fertilization ratio of the phosphorus nutrient, and the reduced fertilization ratio of the potassium nutrient as experimental levels, obtaining a first experimental scheme by using the uniform experimental design; and without reducing the phosphorus nutrient and the potassium nutrient, using the conditioner, the controlled-release nitrogen fertilizer, and the nitrogen nutrient as three experimental factors, and using the dosage of the conditioner, a fertilization ratio of the controlled-release nitrogen fertilizer, and the reduced fertilization ratio of the nitrogen nutrient as experimental levels, obtaining a second experimental scheme by using the orthogonal experimental design.

3. The method according to claim 2, further comprising:

determining the model for reduced fertilization of nitrogen and phosphorus nutrients based on a dosage of a conditioner, a reduced fertilization ratio of a phosphorus nutrient, and a reduced fertilization ratio of a potassium nutrient of the first experimental scheme, and experimental yield data of each experimental processing in the first experimental scheme and the optimized yield data of the optimized fertilization processing; and determining the model for reduced fertilization of nitrogen nutrient based on a dosage of a conditioner, a fertilization ratio of a controlled-release nitrogen fertilizer, and a reduced fertilization ratio of a nitrogen nutrient of the second experimental scheme, and experimental yield data of each experimental processing in the second experimental scheme and the optimized yield data of the optimized fertilization processing.

4. The method according to claim 3, wherein the optimized fertilization processing uses soil testing formula fertilizing technology for fertilization, wherein a nitrogen fertilizer is used in three times as a base fertilizer, a tiller fertilizer, and a spike fertilizer respectively, and a phosphorus fertilizer and a potassium fertilizer are used all at once.

5. The method according to claim 4, wherein determining the basic formula for fertilization comprises determining a type of rice, and the type of rice comprises early rice, middle rice, and late rice.

6. The method according to claim 5, wherein different types of rice correspond to different models for reduced fertilization of phosphorus and potassium nutrients, and in the model for reduced fertilization of phosphorus and potassium nutrients, the dosage of the conditioner is positively correlated with the reduced fertilization ratio of the phosphorus nutrient and the reduced fertilization ratio of the potassium nutrient; and different types of rice correspond to different models for reduced fertilization of nitrogen nutrient, and in the model for reduced fertilization of nitrogen nutrient, the reduced fertilization ratio of the nitrogen nutrient is positively correlated with the dosage of the conditioner, the fertilization ratio of the controlled-release nitrogen fertilizer, and the reduced fertilization ratio of the nitrogen nutrient.

7. The method according to claim 1, wherein the experimental scheme is determined based on a uniform experimental design and an orthogonal experimental design, and the determining the experimental scheme and experimental parameters based on the soil feature and the experimental design comprises:

determining first preferred experimental level sets corresponding to the dosage of the conditioner, the reduced fertilization ratio of the phosphorus nutrient, and the reduced fertilization ratio of the potassium nutrient, respectively, based on the soil feature of the predetermined point;

obtaining a first experimental scheme using the uniform experimental design based on the first preferred experimental level sets; and determining second preferred experimental level sets corresponding to the dosage of the conditioner, a fertilization ratio of a controlled-release fertilizer, and the reduced fertilization ratio of the nitrogen nutrient, respectively, based on the soil feature of the predetermined point; and obtaining a second experimental scheme using the orthogonal experimental design based on the second preferred experimental level sets.

8. The method according to claim 7, further comprising:

determining a fertility difference distribution of the target planting unit based on a soil feature of the predetermined point at one or more time points, the fertility difference distribution comprising a difference value in soil fertility between predetermined sub-regions in the target planting unit; and determining the first preferred experimental level sets and the second preferred experimental level sets based on the soil feature of the predetermined point at the one or more time points and the fertility difference distribution of the predetermined point.

9. The method according to claim 8, wherein the determining the fertility difference distribution of the target planting unit comprises:

determining the fertility difference distribution by means of a difference prediction model based on the soil feature of the predetermined point at the one or more time points, and the difference prediction model being a machine learning model.

10. The method according to claim 9, wherein an input to the difference prediction model further comprises historical experimental data of the target planting unit, and the historical experimental data comprises a historical fertilization frequency and a historical fertilization dosage of different types of fertilizers at different predetermined points of the target planting unit; and the difference prediction model comprises a soil feature embedding layer and a difference predicting layer; the soil feature embedding layer is configured to determine a soil feature embedding vector based on the historical experimental data and the soil feature of the predetermined point at the one or more time points; and the difference predicting layer is configured to determine the fertilizer difference distribution based on the soil feature embedding vector.

11. The method according to claim 9, wherein an input to the difference prediction model comprises a light feature at the one or more time points, and the light feature is determined based on light sensing data collected by a light sensor deployed on a surface of the target planting unit; and the difference prediction model further comprises a light feature embedding layer, and the light feature embedding layer is configured to determine a light feature embedding vector based on the light feature at the one or more time points.

12. A method for generating a fertilizer formula, wherein the method is executed by a processor, comprising:

obtaining a basic formula for fertilization;

obtaining monitoring data based on a monitoring device, the monitoring device being deployed at a predetermined point of a target planting unit;

determining a soil feature of the predetermined point based on the monitoring data;

determining a reduced fertilization ratio of a phosphorus nutrient and a reduced fertilization ratio of a potassium nutrient based on a phosphorus fertilizer price feature, a potassium fertilizer price feature, a soil feature, and a climate feature, and determine a dosage of a conditioner by means of a model for reduced fertilization of phosphorus and potassium nutrients, wherein the phosphorus fertilizer price feature, the potassium fertilizer price feature, the soil feature, and the climate feature are obtained by the processor from one or more Internet of Things units, and the processor is connected to the Internet of Things units in communication connection;

determining a fertilization ratio of a controlled-release fertilizer based on a controlled-release fertilizer price feature, the soil feature, and the climate feature, and determining a reduced fertilization ratio of a nitrogen nutrient by means of a model for reduced fertilization of nitrogen nutrient and the dosage of the conditioner; and determining the fertilizer formula based on the basic formula for fertilization, the reduced fertilization ratio of the phosphorus nutrient, the reduced fertilization ratio of the potassium nutrient, the dosage of the conditioner, a fertilization ratio of a controlled-release nitrogen fertilizer, and the reduced fertilization ratio of the nitrogen nutrient, and storing the fertilizer formula in a storage unit; the model for reduced fertilization of phosphorus and potassium nutrients and the model for reduced fertilization of nitrogen nutrient being obtained by the method according to claim 1.

13. The method according to claim 12, wherein the controlled-release nitrogen fertilizer is resin-coated urea; and the basic formula for fertilization comprises a basic formula for early rice and a basic formula for late or middle rice.

14. A system for generating a fertilizer formula, comprising a processor, wherein the processor is configured to:

obtain a basic formula for fertilization;

obtain monitoring data based on a monitoring device, and the monitoring device is deployed at a predetermined point of a target planting unit;

determine a soil feature of the predetermined point based on the monitoring data;

determine an experimental scheme and experimental parameters based on the soil feature and an experimental design, and the experimental scheme includes one or more experimental processings and an optimized fertilization processing as a control, the experimental parameters comprising a dosage of a conditioner, a fertilization ratio of a controlled-release fertilizer, a reduced fertilization ratio of a nitrogen nutrient, a reduced fertilization ratio of a phosphorus nutrient, and a reduced fertilization ratio of a potassium nutrient;

determine a fertilization dosage based on the experimental parameters and the basic formula for fertilization, and conduct an intelligent planting experiment based on the fertilization dosage and the experimental scheme; wherein the intelligent planting experiment comprises:

obtaining a physicochemical feature at one or more time points corresponding to a predetermined sub-region of the target planting unit based on the monitoring device, and compressing and storing the physicochemical feature within a predetermined compression intensity to obtain a physicochemical feature sequence of the predetermined sub-region, the physicochemical feature comprising at least one of a temperature, a humidity, a pH value, or an EC value, and the predetermined compression intensity being determined based on a residual storage capacity of a storage unit;

determining whether an abnormal sub-region exists based on the physicochemical feature sequence; and in response to a determination that the abnormal sub-region exists, performing a predetermined processing on the abnormal sub-region;

wherein the monitoring device collects the physicochemical feature at a first collection frequency and uploads the physicochemical feature to the processor, the first collection frequency is issued by the processor to the monitoring device within a first predetermined period, the first collection frequency is determined based on a free resource bandwidth of the processor in a future time period, and the first predetermined period is determined based on a change rate of a free resource bandwidth of the processor in a historical time period;

obtain experimental parameters and experimental yield data of each of the one or more experimental processings, and optimized yield data of the optimized fertilization processing, and store the experimental parameters, the experimental yield data and the optimized yield data in the storage unit; and determine a model for reduced fertilization of nitrogen, phosphorus, and potassium nutrients based on the experimental parameters, the experimental yield data, and the optimized yield data through a regression model, and store the model for reduced fertilization of nitrogen, phosphorus, and potassium nutrients in the storage unit, wherein the regression model is extracted by the processor from the storage unit, and the model for reduced fertilization of nitrogen, phosphorus, and potassium nutrients comprises a model for reduced fertilization of phosphorus and potassium nutrients, and a model for reduced fertilization of nitrogen nutrient.

15. The system according to claim 14, wherein the experimental scheme is determined based on a uniform experimental design and an orthogonal experimental design, and the process is further configured to:

without reducing the nitrogen nutrient and without fertilizing a controlled-release nitrogen fertilizer, use the conditioner, the phosphorus nutrient, and the potassium nutrient as three experimental factors, and use the dosage of the conditioner, the reduced fertilization ratio of the phosphorus nutrient, and the reduced fertilization ratio of the potassium nutrient as experimental levels, obtain a first experimental scheme by using the uniform experimental design; and without reducing the phosphorus nutrient and the potassium nutrient, use the conditioner, the controlled-release nitrogen fertilizer, and the nitrogen nutrient as three experimental factors, and use the dosage of the conditioner, a fertilization ratio of the controlled-release nitrogen fertilizer, and the reduced fertilization ratio of the nitrogen nutrient as experimental levels, obtain a second experimental scheme by using the orthogonal experimental design.

16. The system according to claim 15, wherein the processor is further used to:

determine the model for reduced fertilization of nitrogen and phosphorus nutrients based on a dosage of a conditioner, a reduced fertilization ratio of a phosphorus nutrient and a reduced fertilization ratio of a potassium nutrient of the first experimental scheme, experimental yield data of each experimental processing in the first experimental scheme, and the optimized yield data of the optimized fertilization processing; and determine the model for reduced fertilization of nitrogen nutrient based on a dosage of a conditioner, a fertilization ratio of a controlled-release nitrogen fertilizer and a reduced fertilization ratio of a nitrogen nutrient of the second experimental scheme, experimental yield data of each experimental processing in the second experimental scheme and the optimized yield data of the optimized fertilization processing.

17. The system according to claim 14, wherein the experimental scheme is determined based on a uniform experimental design and an orthogonal experimental design, and the processor is further used to:

determine first preferred experimental level sets corresponding to the dosage of the conditioner, the reduced fertilization ratio of the phosphorus nutrient, and the reduced fertilization ratio of the potassium nutrient, respectively, based on the soil feature of the predetermined point;

obtain a first experimental scheme using the uniform experimental design based on the first preferred experimental level sets; and determine second preferred experimental level sets corresponding to the dosage of the conditioner, a fertilization ratio of a controlled-release nitrogen fertilizer, and the reduced fertilization ratio of the nitrogen nutrient, respectively, based on the soil feature of the predetermined point;

obtain a second experimental scheme using the orthogonal experimental design based on the second preferred experimental level sets.

18. The system according to claim 17, wherein the processor is further configured to:

determine a fertility difference distribution of the target planting unit based on a soil feature of the predetermined point at one or more time points, the fertility difference distribution comprising a difference value in soil fertility between predetermined sub-regions in the target planting unit; and determine the first preferred experimental level sets and the second preferred experimental level sets based on the soil feature of the predetermined point at the one or more time points and the fertility difference distribution of the predetermined point.

19. The system according to claim 18, wherein the processor is further configured to:

determine the fertility difference distribution by means of a difference prediction model based on the soil feature of the predetermined point at the one or more time points, and the difference prediction model is a machine learning model.

20. The system according to claim 19, wherein an input to the difference prediction model further comprises historical experimental data of the target planting unit, and the historical experimental data comprises a historical fertilization frequency and a historical fertilization dosage of different types of fertilizers at different predetermined points of the target planting unit; and the difference prediction model comprises a soil feature embedding layer and a difference predicting layer; the soil feature embedding layer is configured to determine a soil feature embedding vector based on the historical experimental data and the soil feature of the predetermined point at the one or more time points; and the difference predicting layer is configured to determine the fertilizer difference distribution based on the soil feature embedding vector.

\* \* \* \* \*